US012678477B2

(12) United States Patent
Barron et al.

(10) Patent No.: US 12,678,477 B2
(45) Date of Patent: Jul. 14, 2026

(54) ANTIVIRAL PEPTOID COMPOSITIONS

(71) Applicant: Maxwell Biosciences, Inc., Austin, TX (US)

(72) Inventors: Annelise E. Barron, Woodside, CA (US); Joshua McClure, West Lake Hills, TX (US); Gill Diamond, Prospect, KY (US); Natalia Molchanova, Kobenhavn V (DK)

(73) Assignee: Maxwell Biosciences, Inc., Austin, TX (US)

( * ) Notice: Subject to any disclaimer, the term of this patent is extended or adjusted under 35 U.S.C. 154(b) by 1121 days.

(21) Appl. No.: 17/640,322

(22) PCT Filed: Sep. 30, 2020

(86) PCT No.: PCT/US2020/053425
§ 371 (c)(1),
(2) Date: Mar. 3, 2022

(87) PCT Pub. No.: WO2021/046562
PCT Pub. Date: Mar. 11, 2021

(65) Prior Publication Data
US 2022/0401513 A1 Dec. 22, 2022

Related U.S. Application Data

(60) Provisional application No. 62/895,486, filed on Sep. 3, 2019.

(51) Int. Cl.
| | |
|---|---|
| *A61K 38/10* | (2006.01) |
| *A61K 38/05* | (2006.01) |
| *A61K 38/06* | (2006.01) |
| *A61K 38/07* | (2006.01) |
| *A61K 38/08* | (2019.01) |
| *A61P 31/04* | (2006.01) |
| *A61P 31/12* | (2006.01) |

(52) U.S. Cl.
CPC .............. *A61K 38/10* (2013.01); *A61K 38/05* (2013.01); *A61K 38/06* (2013.01); *A61K 38/07* (2013.01); *A61K 38/08* (2013.01); *A61P 31/04* (2018.01); *A61P 31/12* (2018.01)

(58) Field of Classification Search
CPC ........ A61K 38/10; A61K 38/05; A61K 38/06; A61K 38/07; A61K 38/08; A61K 31/198; A61K 38/00; A61P 31/04; A61P 31/12
See application file for complete search history.

(56) References Cited

U.S. PATENT DOCUMENTS

| | | | |
|---|---|---|---|
| 8,445,632 B2 | 5/2013 | Barron et al. | |
| 2013/0065833 A1* | 3/2013 | Barron .................. | C07K 14/785 514/21.4 |
| 2013/0109627 A1 | 5/2013 | Barron et al. | |
| 2022/0213144 A1* | 7/2022 | Molchanova ............ | C07K 7/06 |

FOREIGN PATENT DOCUMENTS

| | | |
|---|---|---|
| WO | 2003/015714 A2 | 2/2003 |
| WO | 2017/192756 A1 | 11/2017 |
| WO | 2020/223581 A1 | 11/2020 |

OTHER PUBLICATIONS

Search Report, European Application No. 20859817.7, mailing date: Oct. 26, 2023, 16 pages.
Simon R J et al: "Peptoids; a modular approach to drug discovery", Proceedings of the National Academy of Sciences, National Academy of Sciences, vol. 89, No. 20, Oct. 15, 1992, pp. 9367-9371.
Thomas Klimkait et al: "Rational optimization of a HIV-1 Tat inhibitor: Rapid progress on combinatorial lead structures", Biotechnology and Bioengineering, vol. 61, No. 3, Jan. 1, 1999, pp. 155-168.
Junjie Fu et al.: "Design-Based Peptidomimetic Ligand Discovery to Target HIV TAR RNA Using Comparative Analysis of Different Docking Methods", Current HIV Research, vol. 14, No. 6, Nov. 2, 2016, pp. 476-483.
Hamy François et al.: "Merged Screening for Human Immunodeficiency Virus Tat and Rev Inhibitors", Slas Discovery: Advancing Life Sciences R&D, vol. 6, No. 3, Jun. 1, 2001, pp. 179-187.
Hamy F et al: "An inhibitor of the Tat/TAR RNA interaction that effectively suppresses HIV-1 replication", Proceedings of the National Academy of Sciences, National Academy of Sciences, vol. 94, No. 8, Apr. 15, 1997, pp. 3548-3553.
Venkitasamy Kesavan et al: "A New Class of RNA-Binding Oligomers: Peptoid Amide and Ester Analogues", Bioconjugate Chemistry, vol. 13, No. 6, Nov. 1, 2002, pp. 1171-1175.

(Continued)

*Primary Examiner* — Erinne R Dabkowski
(74) *Attorney, Agent, or Firm* — McDermott Will & Schulte LLP

(57) ABSTRACT

A method is provided for treating a subject for a viral infection. The method includes diagnosing the subject as having a viral infection, and administering a pharmaceutically effective amount of a pharmaceutical composition to the subject. The pharmaceutical composition includes a poly-N-substituted glycine compound of a formula $$A{-}(X{-}Y\text{-}Z)_{\overline{n}}{-}B,$$

wherein A is a terminal N-alkyl substituted glycine residue; n is an integer; B is selected from the group consisting of $NH_2$, one and two N-substituted glycine residues, and wherein said one and two N-substituted glycine residues have N-substituents which are independently selected from natural $\alpha$-amino acid side chain moieties, isomers and carbon homologs thereof; X, Y and Z are independently selected from the group consisting of N-substituted glycine residues, wherein said N-substituents are independently selected from the group consisting of natural $\alpha$-amino acid side chain moieties, isomers and carbon homologs thereof, and proline residues. In some embodiments, at least one of A, B, X, Y and Z contains a halogen-bearing moiety.

1 Claim, 27 Drawing Sheets

(56) References Cited

OTHER PUBLICATIONS

PCT Transmittal, International Search Report and written Opinion of the International Searching Authority for International application No. PCT/US2020/053425, mailing date: Feb. 8, 2021, 15 pages.

PCT International Preliminary Report on Patentability with Written Opinion for International application No. PCT/US2020/053425, Issued Mar. 8, 2022, 9 pages.

Chongsiriwatana et al. "Peptoids that mimic the structure, function, and mechanism of helical antimicrobial peptides," Proceedings of the National Academy of Sciences of the USA, Feb. 26, 2008 (Feb. 26, 2008). vol. 105, 1ss. 8, pp. 2794-2799. entire document.

Dohm et al. "Peptoids: Bio-Inspired Polymers as Potential Pharmaceuticals," Current Pharmaceutical Design, Dec. 31, 2011 (Dec. 31, 2011), vol. 17, No. 25, pp. 2732-2747. entire document.

Molchanova, Natalia et al., "Halogenation as a tool to tune antimicrobial activity of peptoids", Scientific Reports, Sep. 9, 2020., vol. 10, No. 14805.

* cited by examiner

FIG. 1

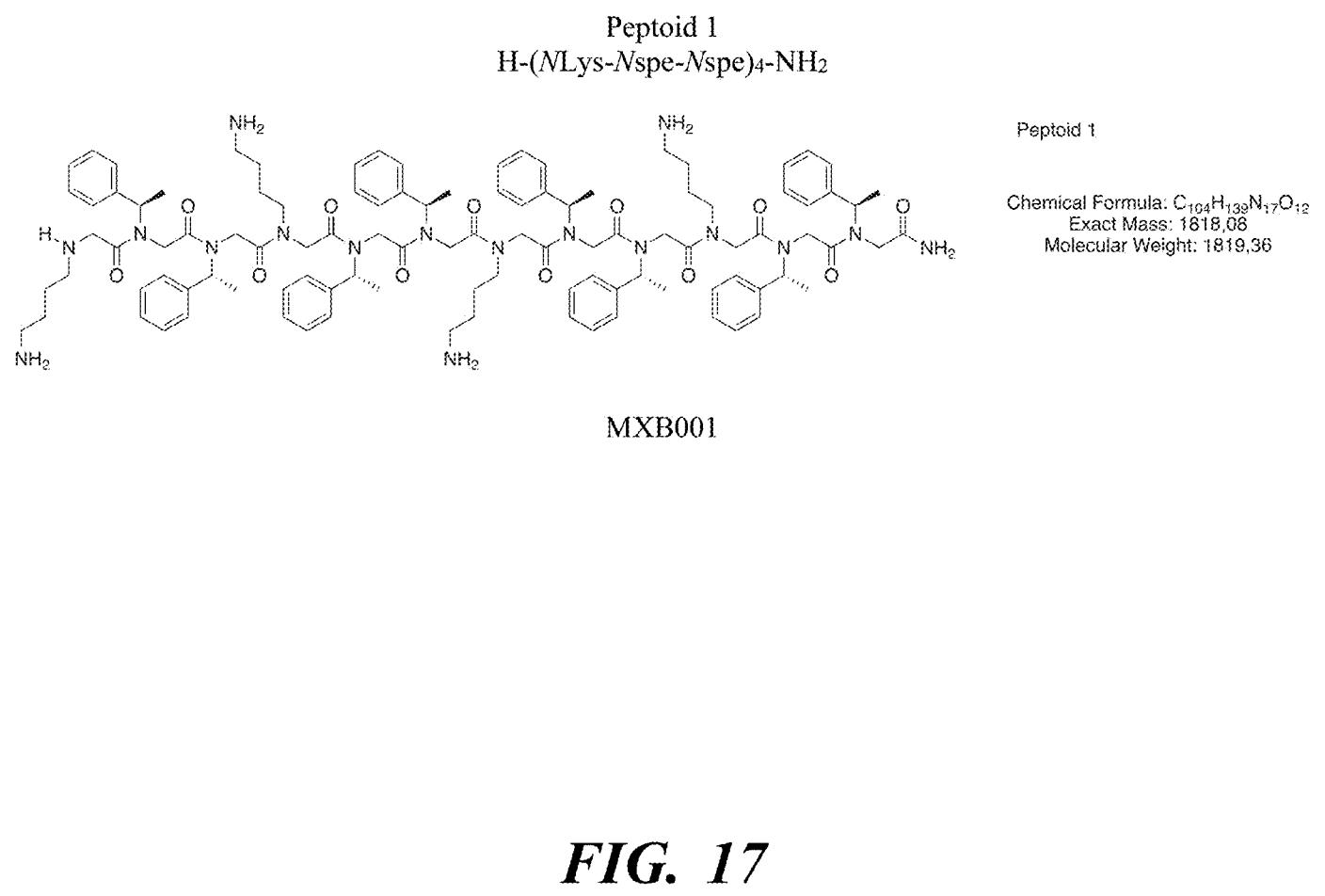

Peptoid 1

H-(*N*Lys-*N*spe-*N*spe)₄-NH₂

Peptoid 1

Chemical Formula: C₁₀₄H₁₃₈N₁₇O₁₂
Exact Mass: 1818.08
Molecular Weight: 1819.36

MXB001

*FIG. 17*

Figure 18:
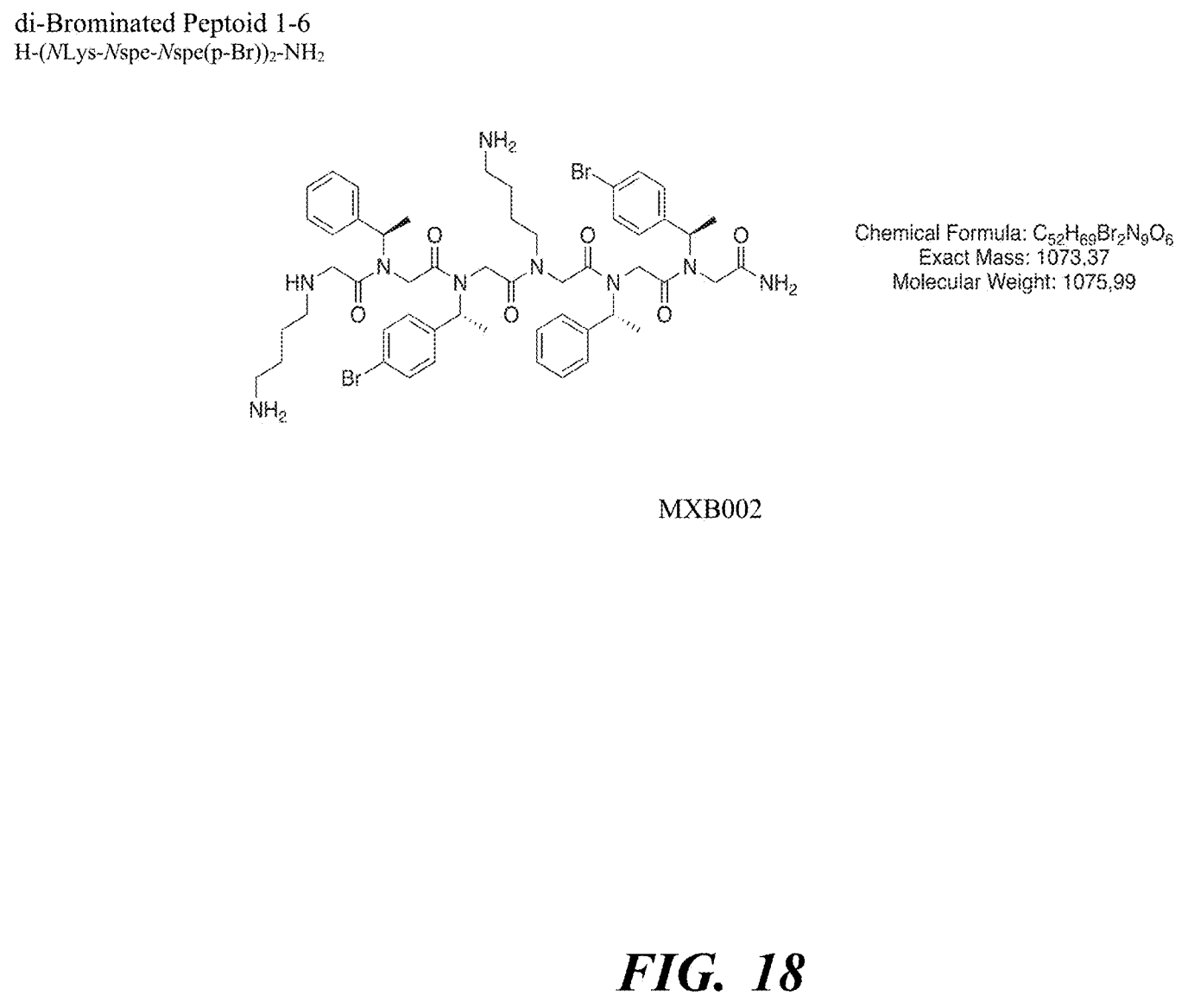

Chemical Formula: C$_{52}$H$_{69}$Br$_2$N$_9$O$_6$
Exact Mass: 1073.37
Molecular Weight: 1075.99

MXB002 di-Brominated Peptoid 1-6
H-(NLys-Nspe-Nspe(p-Br))$_2$-NH$_2$

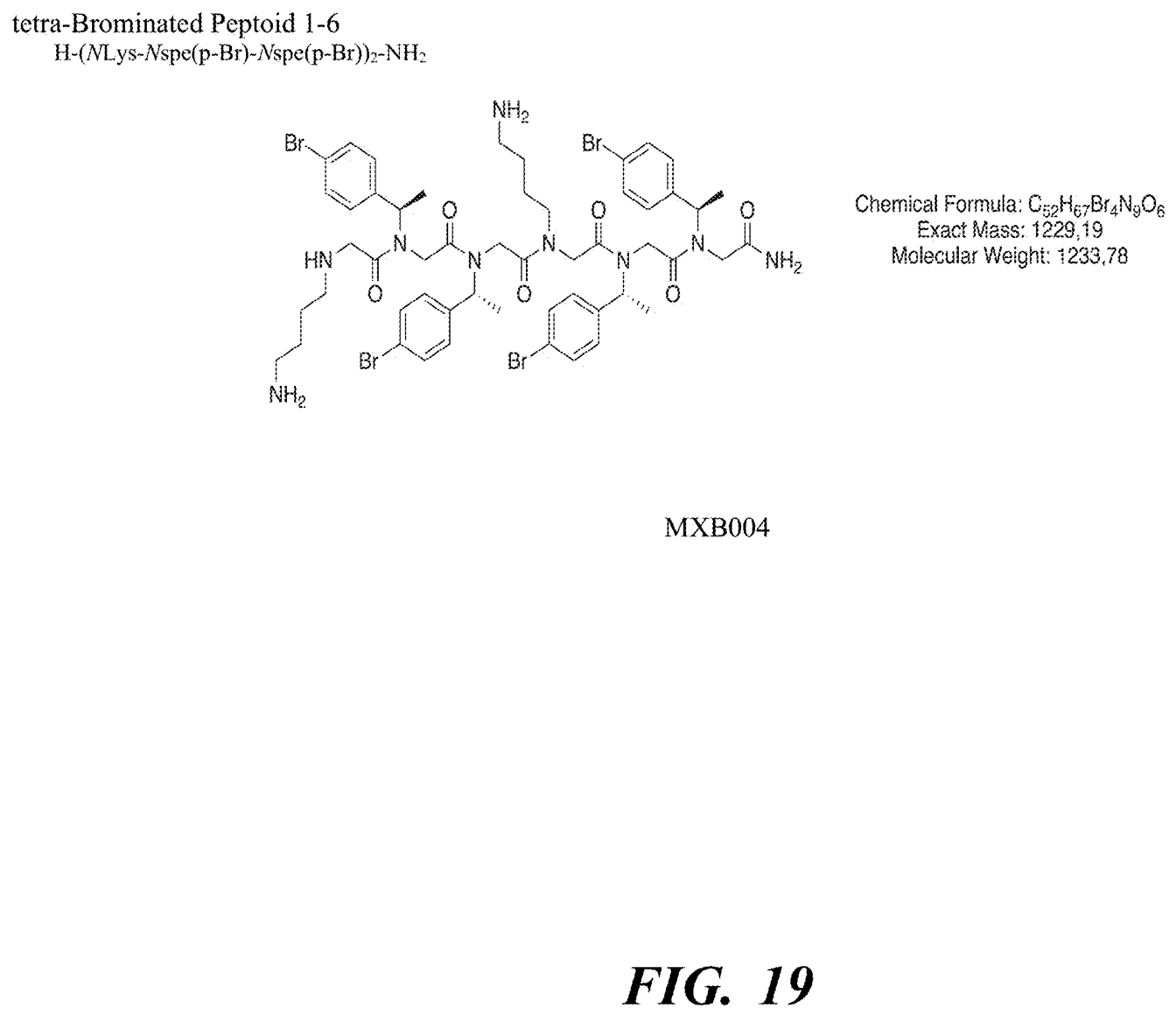

*FIG. 18* tetra-Brominated Peptoid 1-6
H-(NLys-Nspe(p-Br)-Nspe(p-Br))₂-NH₂

Chemical Formula: $C_{52}H_{67}Br_4N_9O_6$
Exact Mass: 1229.19
Molecular Weight: 1233.78

MXB004

*FIG. 19*

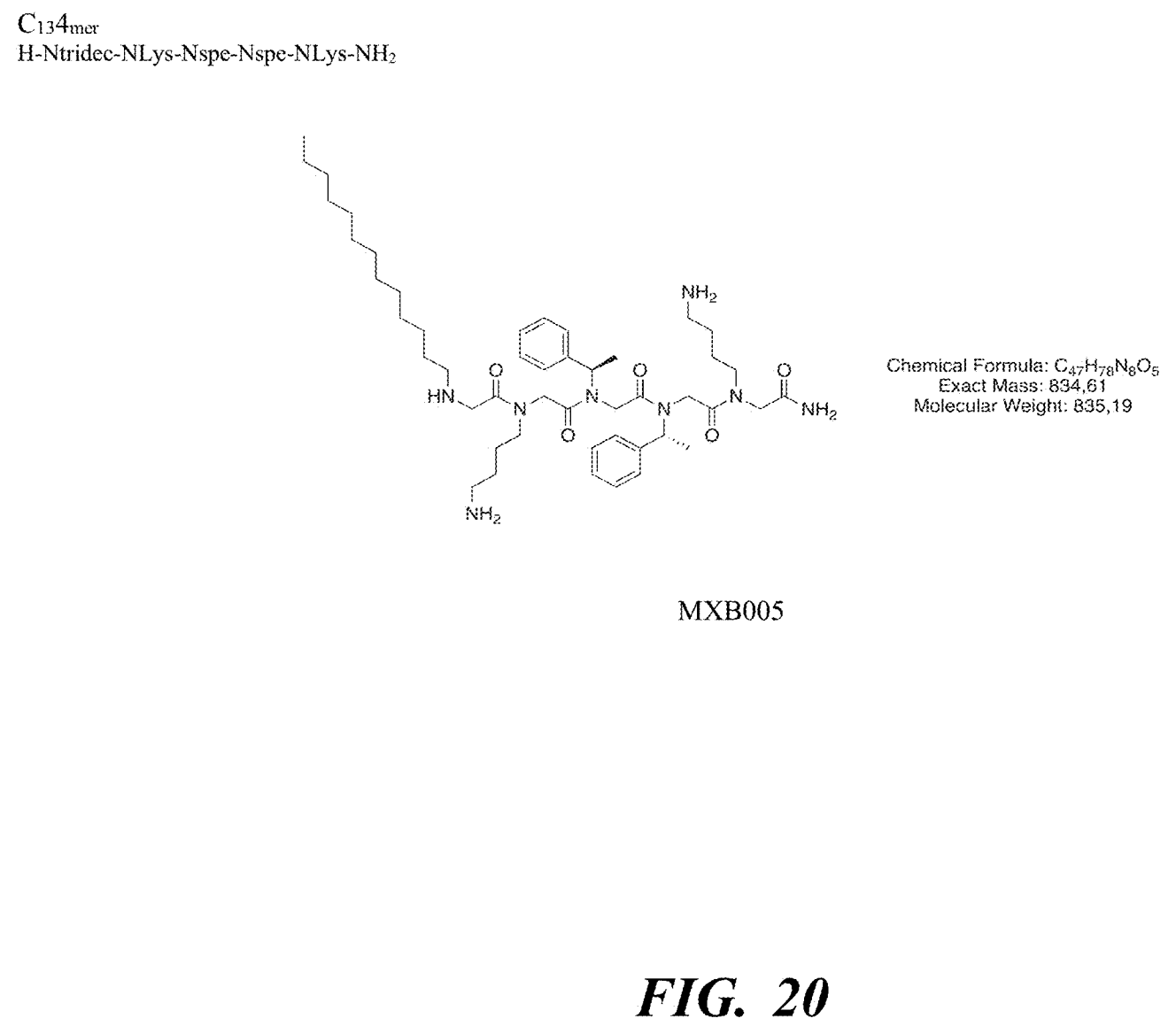

Chemical Formula: $C_{47}H_{78}N_8O_5$
Exact Mass: 834,61
Molecular Weight: 835,19

MXB005

C$_{134}$mer
H-Ntridec-NLys-Nspe-Nspe-NLys-NH$_2$

*FIG. 20*

Figure 21:
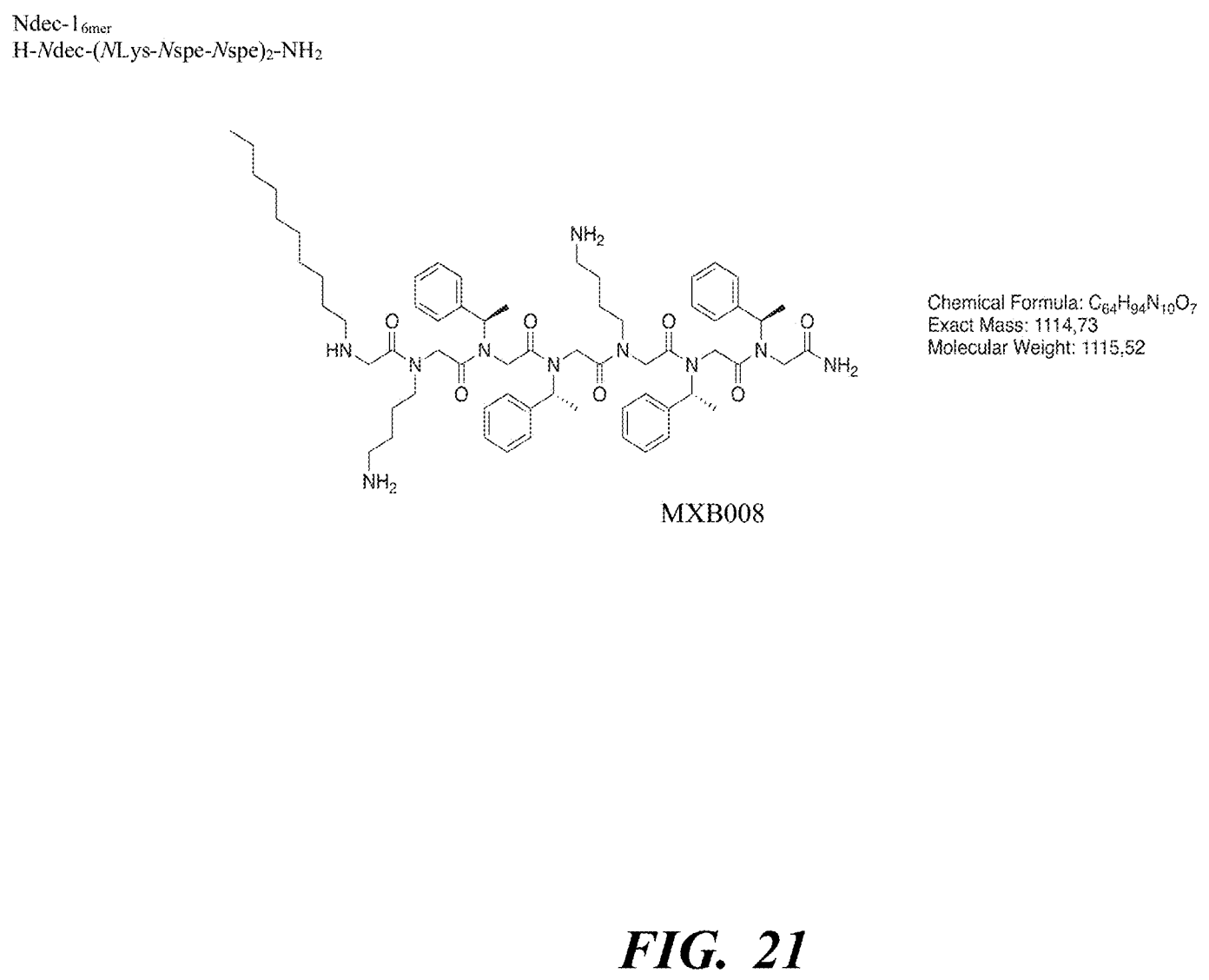

Chemical Formula: $C_{64}H_{94}N_{10}O_7$
Exact Mass: 1114.73
Molecular Weight: 1115.52

MXB008

Ndec-1$_{6mer}$
H-$N$dec-($N$Lys-$N$spe-$N$spe)$_2$-NH$_2$

Figure 22:
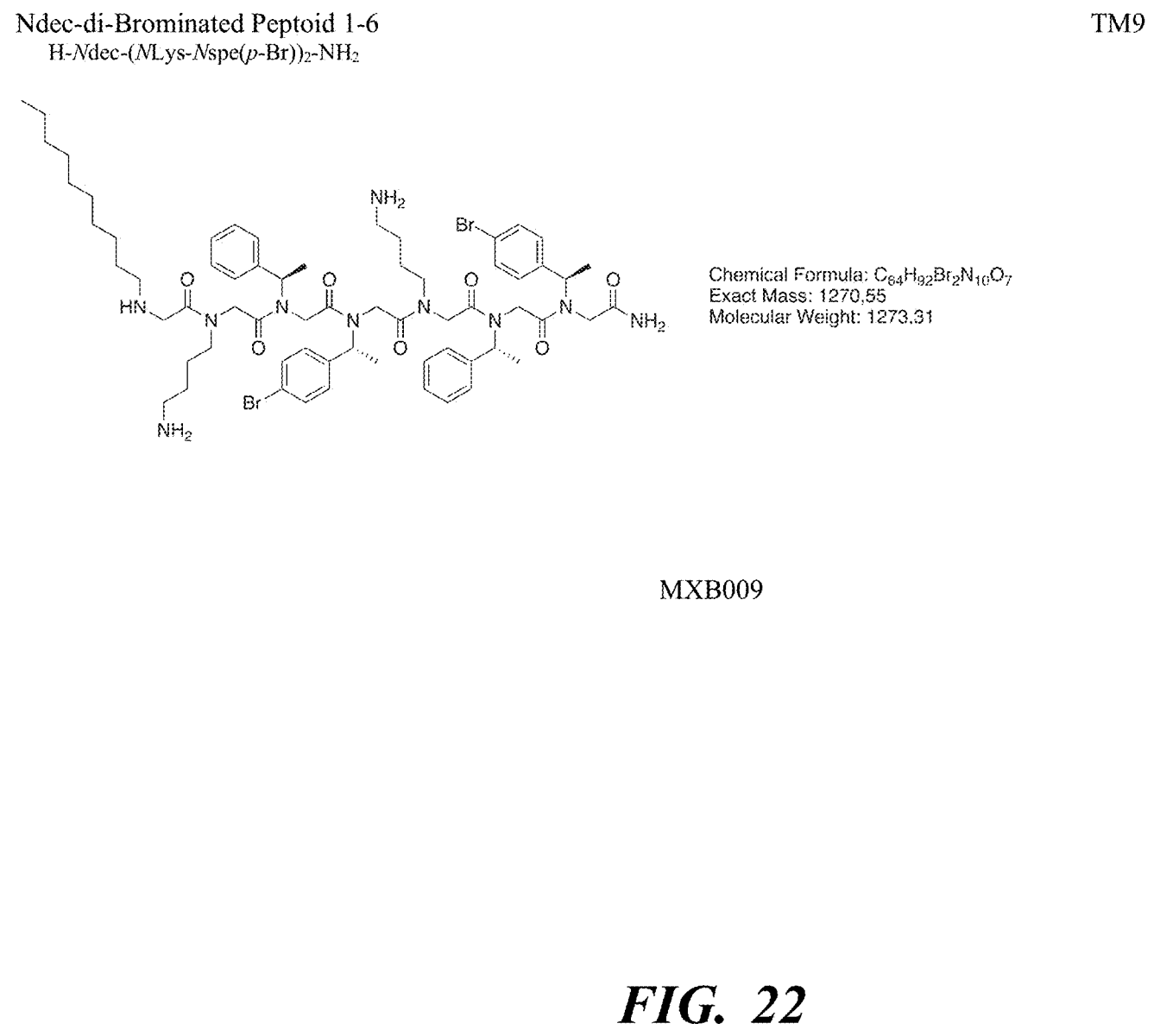

Ndec-di-Brominated Peptoid 1-6
H-Ndec-(NLys-Nspe(p-Br))₂-NH₂

Chemical Formula: $C_{64}H_{92}Br_2N_{10}O_7$
Exact Mass: 1270.55
Molecular Weight: 1273.31

MXB009

Ndec-di-Brominated Peptoid 1-6

H-Ndec-(NLys-Nspe(p-Br))₂-NH₂

Chemical Formula: C₆₄H₉₂Br₂N₁₀O₇
Exact Mass: 1270.55
Molecular Weight: 1273.31

MXB011

Chemical Formula: C₅₈H₈₁Br₂N₁₁O₇
Exact Mass: 1201.47
Molecular Weight: 1204.16 di-Brominated Peptoid 1-6-NLys
H-(NLys-Nspe-Nspe(p-Br))₂-NLys-NH₂

MXB012

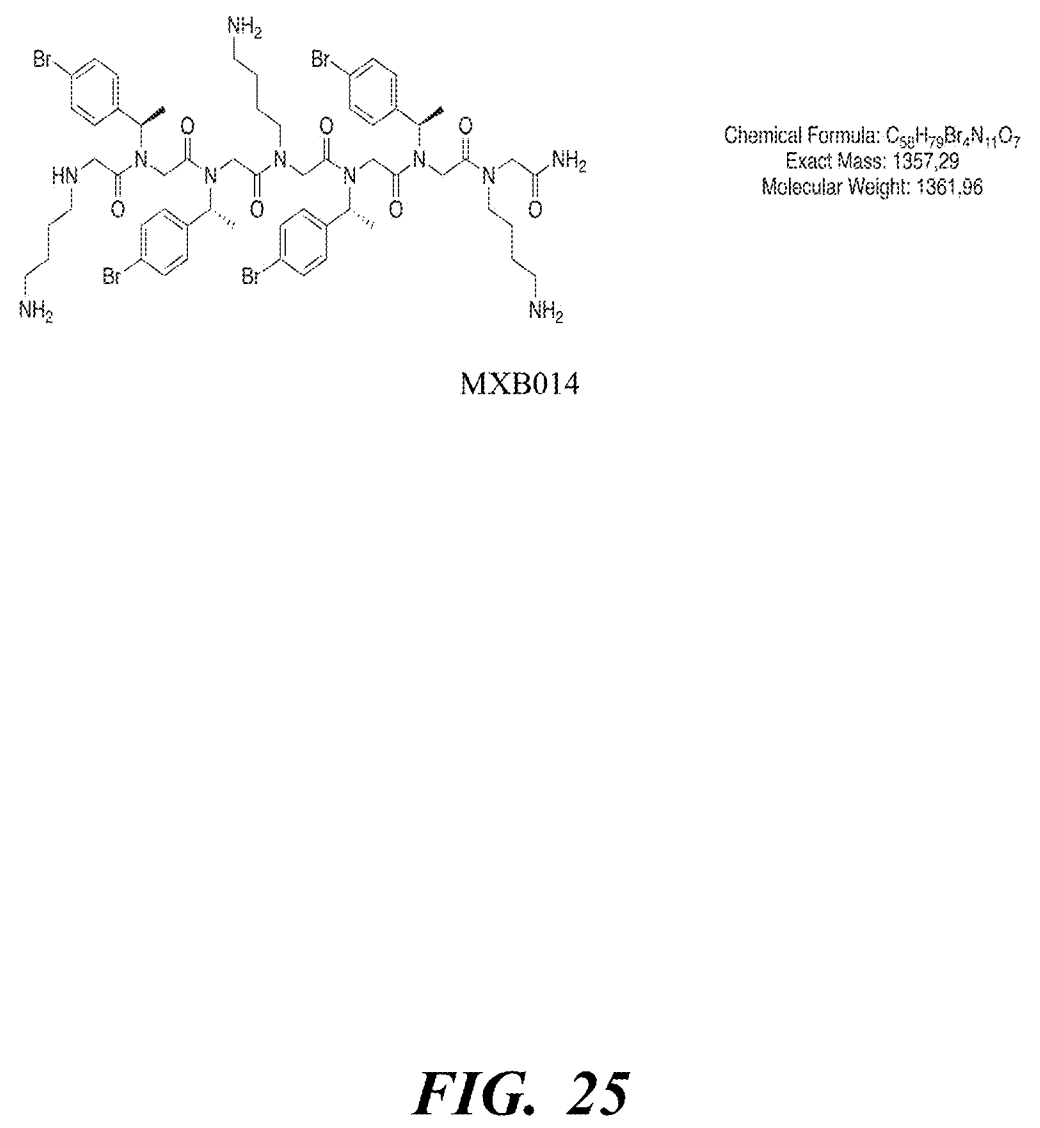

Chemical Formula: $C_{58}H_{79}Br_4N_{11}O_7$
Exact Mass: 1357.29
Molecular Weight: 1361.96

MXB014

*FIG. 25*

Chemical Formula: $C_{53}H_{90}N_{10}O_6$
Exact Mass: 962.70
Molecular Weight: 963.37

MXB015

$C_{13}4_{mer}$
H-Ntridec-NLys-Nspe-Nspe-NLys-NLys-NH$_2$

Chemical Formula: C₇₀H₁₀₄Br₂N₁₂O₈
Exact Mass: 1398.65
Molecular Weight: 1401.49

MXB019

Ndec-di-Brominated Peptoid 1-6-NLys
H-Ndec-(NLys-Nspe(p-Br))₂-NLys-NH₂

ANTIVIRAL PEPTOID COMPOSITIONS

CROSS-REFERENCE TO RELATED APPLICATION

The present application is a national stage filing of PCT/US20/53425, filed on Sep. 30, 2020, which has the same title and the same inventors, and which is incorporated herein by reference in its entirety; which claims priority to U.S. Provisional No. 62/895,486, filed Sep. 3, 2019, having the same title, and having the same inventors, and which is incorporated herein by reference in its entirety.

FIELD OF THE DISCLOSURE

The present disclosure relates generally to antiviral compositions, and more particularly, to antiviral peptoid compositions.

BACKGROUND OF THE DISCLOSURE

Within the last couple of decades, a significant amount of research has focused on the use of antimicrobial peptides in the treatment of multi-drug resistant bacteria. Natural antimicrobial peptides (AMPs) are known to defend a wide array of organisms against bacterial pathogens. These AMPs have shown potential as supplements for (or replacements of) conventional antibiotics, since few bacteria have evolved resistance to them.

AMPs destroy bacteria in various ways. Some AMPs kill bacteria by permeating the cytoplasmic membrane and causing depolarization or leakage of internal cell materials. Other AMPs function by targeting anionic bacterial constituents, such as DNA, RNA, or cell wall components. Bacterial resistance to AMPs is rare, possibly because AMPs have evolved along with the resistance mechanisms that are designed to evade them. Moreover, the targets of many AMPs (such as bacterial plasma membranes and anionic intracellular macromolecules) are sufficiently general that changes to the sequence of the AMP can be made to subvert resistance, without having any significant adverse impact on overall functionality.

Although AMPs have been actively studied for decades, they have yet to achieve widespread clinical use. This is due, in part, to the vulnerability of many peptide therapeutics to rapid in vivo degradation, which dramatically reduces their bioavailability.

The foregoing problems have led to the development of peptidomimetics, which are small, protein-like chains designed to mimic a peptide. Peptidomimetics may be made by modifying an existing peptide, or may be based on similar systems that mimic peptides, such as peptoids and β-peptides.

Peptoids (poly-N-substituted glycines) are isomers of peptides in which side chains are attached to the backbone amide nitrogen rather than to the α-carbon. Antimicrobial peptoids have been described, for example, in U.S. Pat. No. 8,445,632 (Barron et al.), entitled "Selective Poly-N-Substituted Glycine Antibiotics", which is incorporated herein by reference in its entirety.

Peptoids are particularly well-suited for AMP mimicry. Peptoids are easily synthesized using conventional peptide synthesis equipment, and provide access to diverse sequences at relatively low cost. Submonomer synthetic methods are known that may be utilized to impart a wide variety of chemical functionalities to peptoids. Consequently, peptoids are highly and finely tunable. Furthermore, they are protease-resistant, and can be designed to form amphipathic helices that resist thermal and chaotropic denaturation.

SUMMARY OF THE DISCLOSURE

In one aspect, a method for treating a subject for a viral infection is provided. The method comprises (a) diagnosing the subject as having a viral infection; and (b) administering a pharmaceutically effective amount of a pharmaceutical composition to the subject, the pharmaceutical composition comprising a poly-N-substituted glycine compound of a formula $$A\text{---}(X\text{---}Y\text{-}Z)_n\text{---}B$$

wherein
A is a terminal N-alkyl substituted glycine residue,
n is an integer,
B is selected from the group consisting of $NH_2$, one and two N-substituted glycine residues, and wherein said one and two N-substituted glycine residues have N-substituents which are independently selected from natural α-amino acid side chain moieties, isomers and carbon homologs thereof, and
X, Y and Z are independently selected from the group consisting of N-substituted glycine residues, wherein said N-substituents are independently selected from the group consisting of natural α-amino acid side chain moieties, isomers and carbon homologs thereof, and proline residues.

In another aspect, a method for treating a subject for a viral infection. The method comprises (a) diagnosing the subject as having a viral infection; and (b) administering a pharmaceutically effective amount of a pharmaceutical composition to the subject, the pharmaceutical composition comprising a poly-N-alkyl substituted glycine compound of a formula $$H\text{---}N_R\text{---}(X\text{---}Y\text{-}Z)_n\text{---}B$$

wherein
B is selected from $NH_2$ and X',
$N_R$, X, Y, Z and X' are independently selected from N-substituted glycine residues containing N-substituents, wherein said N-substituents of said N-substituted glycine residues are independently selected from natural α-amino acid side chain moieties, isomers and carbon homologs thereof, and proline residues,
n is an integer, and
R is an N-alkyl substituent of said $N_R$ glycine residue, said substituent selected from about $C_4$ to about $C_{20}$ linear, branched and cyclic alkyl moieties.

In a further aspect, a method is provided for treating a subject for a viral infection. The method comprises (a) diagnosing the subject as having a viral infection; and (b) administering a pharmaceutically effective amount of a pharmaceutical composition to the subject, the pharmaceutical composition comprising a poly-N-substituted glycine compound comprising an N-terminal N-alkyl substituted glycine residue, where said alkyl substituent is selected from about $C_4$ to about $C_{20}$ linear, branched and cyclic alkyl moieties; a C-terminus selected from $NH_2$, one and two N-substituted glycine residues, said N-substituents independently selected from α-amino acid side chain moieties and carbon homologs thereof; and 2 to about 15 monomeric residues between said N- and C-termini, each said residue independently selected from proline residues and N-substituted glycine residues, said N-substituents independently selected from natural α-amino acid side chain moieties, isomers and carbon homologs thereof, at least one said monomeric residue is $N_{Lys}$ and at least one said N-substituent is chiral, said monomeric residues selected to provide said compound a non-periodic sequence of monomeric residues.

In still another aspect, a method is provided for treating a subject for an infection. The method comprises diagnosing the subject as having an infection involving at least one viral pathogen and at least one bacterial pathogen; and administering a pharmaceutically effective amount of a pharmaceutical composition to the subject, the pharmaceutical composition comprising at least one peptoid. The at least one peptoid is preferably a poly-N-substituted glycine compound, and is preferably effective in simultaneously treating both the at least one viral pathogen and at least one bacterial pathogen.

BRIEF DESCRIPTION OF THE DRAWINGS

Figure 1:
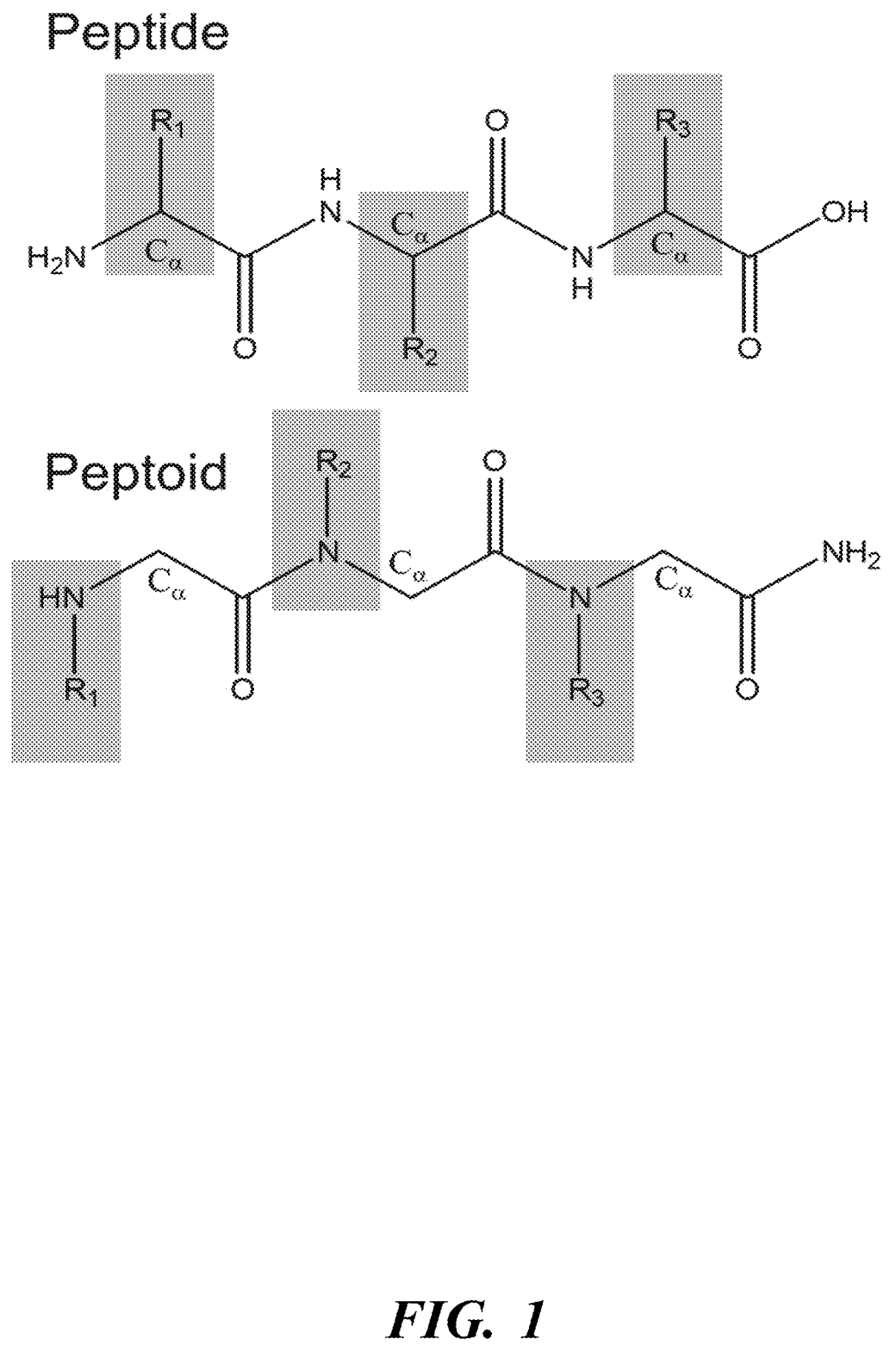

FIG. 1 is an illustration of the structural similarities and differences between peptides and peptoids.

FIGS. 15-27 depict the structures of several peptoids in accordance with the teachings herein.

DETAILED DESCRIPTION

Figure 2:
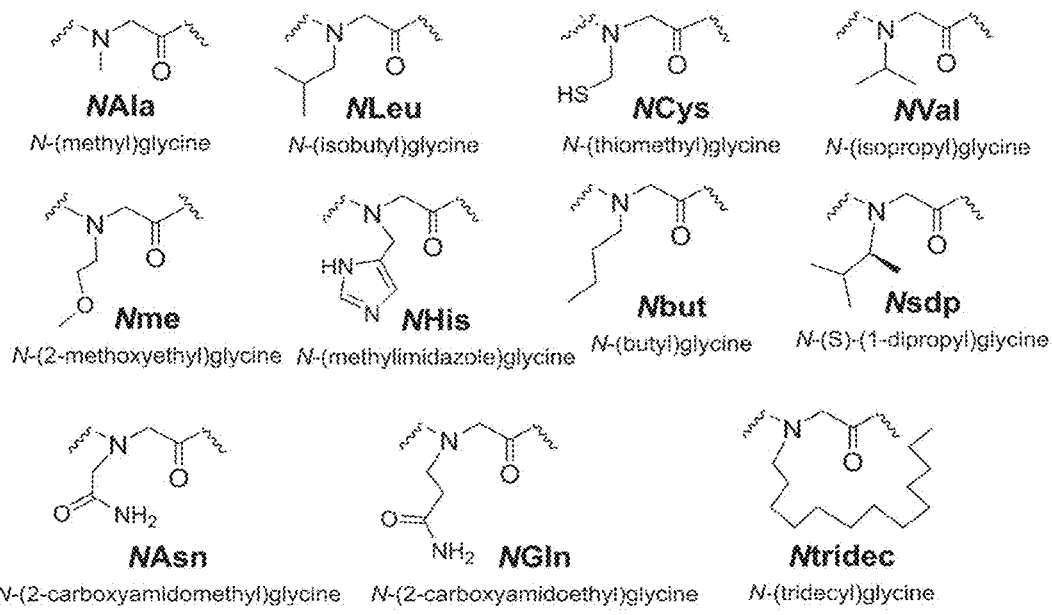
FIG. 2 is an illustration of the structures of biomimetic oligopeptoid monomers used in the antimicrobial peptide mimics disclosed herein.
Figure 2:
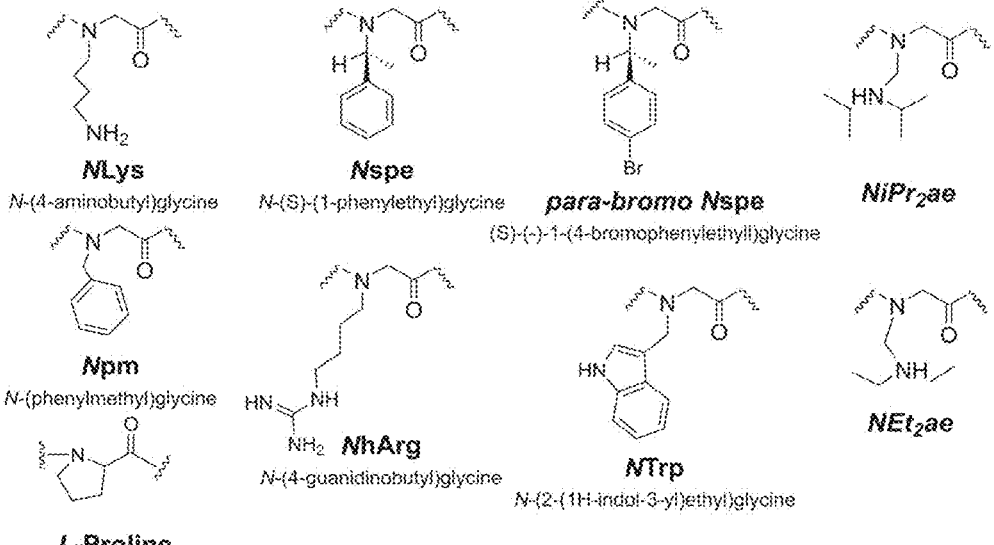

Most bacterial infections can be treated with suitable antibiotics, such as penicillin. However, antibiotics are typically useless against viral infections, including influenza, the common cold, and hemorrhagic fevers such as Ebola.

This difference in efficacy of antibiotics towards these pathogens arises from the fundamental differences between bacteria and viruses themselves. In particular, bacteria are relatively complex, single-celled organisms which can reproduce on their own. Bacteria typically consist of a rigid cell wall, and a thin, rubbery membrane surrounding the fluid inside the cell. By contrast, viruses are much smaller than bacteria. Most viruses consist only of a protein coat and a core of genetic material (either RNA or DNA), and cannot survive independently of a host. Viruses typically reproduce by attaching themselves to host cells and reprogramming those cells to make new instances of the virus.

Many antiviral drugs work by targeting the mechanisms of viral replication. However, the long-term efficacy of such drugs frequently depends on the robustness of the treatment. In particular, if the treatment is sufficiently robust and viral fitness is sufficiently impaired, no viral genomes will be successfully replicated, and the effectiveness of the drug may continue indefinitely. However, if the treatment is less robust and some genomes replicate, selective pressure may result in rapid adaptation by the virus toward resistance. This process is exacerbated by the large population sizes and high rates of mutation that characterize many viruses. Consequently, in such cases, if resistance-conferring polymorphisms do not already exist in the virus population at the onset of treatment, they will likely arise soon thereafter.

The history of the herpes simplex virus (HSV) provides a sobering illustration of the foregoing principles. This virus, which is a member of the Herpesviridae family, is a significant human pathogen that results in mucocutaneous lesions in the oral cavity or genital infections. An estimated 60%-95% of the population is infected by at least one of these viruses, thus making HSV infections are among the most common of human diseases. HSV leads to diseases that range from mild conditions to severe infections, such as cold sores, keratitis, corneal blindness, and encephalitis, and may result in life-threatening infections in immunocompromised individuals. HSV infections also increase the risk to patients of developing human immunodeficiency virus (HIV) infections, and thus contribute to the HIV epidemic. There is also mounting evidence that HSV infections may be associated with the pathogenesis of Alzheimer's disease.

Three classes of drugs are currently approved for treatment of HSV infections. All three—acyclic guanosine analogues, acyclic nucleotide analogues, and pyrophosphate analogues—target viral DNA replication. The standard therapy for the management of HSV infections includes acyclovir (ACV) and penciclovir (PCV) with their respective prodrugs valacyclovir and famciclovir. These compounds are phosphorylated by the viral thymidine kinase (TK) and then by cellular kinases. The triphosphate forms selectively inhibit the viral DNA polymerase (DNA pol) activity.

ACV and related nucleoside analogues have demonstrated some efficacy in treating HSV infections. However, while acyclovir treatment can reduce the symptoms and shorten the duration of the lesions, it is only effective when given orally, and only reduces transmission by 50%.

Moreover, the emergence of strains of the HSV virus which exhibit drug resistance to ACV has created a barrier for the treatment of HSV infections, especially in the case of immunocompromised patients. This has led to a call for new antiherpetic compounds with different mechanisms of action. See, e.g., Jocelyne Piret and Guy Boivin, "Resistance of Herpes Simplex Viruses to Nucleoside Analogues: Mechanisms, Prevalence, and Management", Antimicrob Agents Chemother. 2011 February; 55(2): 459-472.

There is thus a need in the art for a new class of pharmaceutical treatments and compositions which are effective against viral pathogens, including HSV. There is further a need for such treatments and pharmaceutical compositions which function by different mechanisms than conventional treatments, and which are less susceptible to the development of resistance by viral pathogens. There is also a need in the art for such pharmaceutical compositions which have low toxicity, and which do not undergo rapid in vivo degradation. These and other needs may be met with the compositions and methodologies disclosed herein.

It has now been found that some or all of the foregoing needs may be met with the peptoid (oligomers of N-substituted glycines) compositions disclosed herein. These compositions have been found to exhibit surprising and unexpected activity against various viral agents. Without wishing to be bound by theory, the surprising effectiveness of at least some peptoids against viral pathogens arises from an apparent equivalence of mechanism of their antiviral activity to the Human Cathelicidin antimicrobial peptide LL-37. In particular, like LL-37, these peptoids exhibit a similar ability to pass through viral membranes and to bind to DNA or RNA. Consequently, these peptoids offer potential efficacy against the same viruses that LL-37 is active against including, without limitation, HSV-1, HSV-2, Vaccinia virus, Respiratory Syncytial Virus (RSV), the Hepatitis C Virus (HCV), influenza A viruses (IAV), corona viruses (including SARS-COV-2, the virus responsible for the coronavirus disease COVID-19) and the HIV-1 virus.

ventive treatment. Current therapies are ineffective at preventing and treating oral lesions of HSV-1. Hence, the compositions and methodologies disclosed herein represent the first, clinical application of peptoids towards treatment of such lesions.

Thirdly, novel animal models for HSV infections may be utilized for real-time imaging and evaluation of new treatments. This work on peptoids will help guide the future testing and development of other novel therapies for viral infections.

Reference is made therein to several peptoids made in accordance with the teachings herein. These peptoids have the designations and structures depicted in TABLE 1 below. It is to be noted that the letter precursors TM and MXB may be used interchangeably in the designations of these peptoids (that is, for example, MXB016 and TM016 refer to the same peptoid).

TABLE 1

| Designations and Structures of Peptoids | | | |
|---|---|---|---|
| Peptoid | Structure | Chemical Formula | M.W. |
| MXB001 | H-(NLys-Nspe-Nspe)$_4$-NH$_2$ | C$_{104}$H$_{139}$N$_{17}$O$_{12}$ | 1819.36 |
| MXB002 | H-(NLys-Nspe-Nspe(p-Br))$_2$—NH$_2$ | C$_{52}$H$_{69}$N$_9$O$_6$ | 1075.99 |
| MXB003 | H- NLys-Nspe-Nspe-NLys-Nspe-Nspe(p-Br)—NH$_2$ | | |
| MXB004 | H-((NLys-Nspe(p-Br)-Nspe(p-Br))$_2$—NH$_2$ | C$_{52}$H$_{67}$Br$_4$N$_9$O$_6$ | 1233.78 |
| MXB005 | H-Ntridec-NLys-Nspe-Nspe-NLys-NH$_2$ | C$_{47}$H$_{78}$N$_8$O$_5$ | 835.19 |
| MXB007 | H-(NLys-Nspe-Nspe)$_3$-NLys-Nspe-NH$_2$ | | |
| MXB008 | H-(NLys-Nspe-Nspe)$_2$-NH$_2$ | C$_{64}$H$_{94}$N$_{10}$O$_7$ | 1115.52 |
| MXB009 | H-Ndec-(NLys-Nspe-Nspe)$_2$-NH$_2$ | C$_{64}$H$_{92}$N$_{10}$O$_7$ | 1273.31 |
| MXB010 | H- Ndec-(NLys-Nspe-Nspe(p-Br))$_2$—NH$_2$ | | |
| MXB011 | H- Ntridec-(NLys-Nspe-Nspe(p-Br))$_2$—NH$_2$ | C$_{110}$H$_{151}$N$_{19}$O$_{13}$ | 1947.54 |
| MXB012 | H-(NLys-Nspe-Nspe)$_4$-NLys-NH$_2$ | C$_{58}$H$_{81}$Br$_2$N$_{11}$O$_7$ | 1204.16 |
| MXB013 | H-(NLys-Nspe-Nspe(p-Br))$_2$-NLys-NH$_2$ | | |
| MXB014 | H-NLys-Nspe-Nspe-NLys-Nspe-Nspe(p-Br)-NLys-NH$_2$ | C$_{58}$H$_{79}$Br$_4$N$_{11}$O$_7$ | 1361.96 |
| MXB015 | H-(NLys-Nspe(p-Br)-Nspe(p-Br))$_2$-NLys-NH$_2$ | C$_{53}$H$_{90}$N$_{10}$O$_6$ | 962.70 |
| MXB016 | H-Ntridec-NLys-Nspe-Nspe-NLys-NLys-NH$_2$ | | |
| MXB017 | H-(NLys-Nspe-Nspe)$_3$-NLys-Nspe-NLys-NH$_2$ | | |
| MXB018 | H-(NLys-Nspe-Nspe)$_2$-NLys-NH$_2$ | | |
| MXB019 | H-Ndec-(NLys-Nspe-Nspe)$_2$-NLys-NH$_2$ | C$_{70}$H$_{104}$Br$_2$N$_{12}$O$_8$ | 1401.49 |
| MXB020 | H- Ndec-(NLys-Nspe-Nspe(p-Br))$_2$-NLys-NH$_2$ | | 1440 |
| MXB021 | H- Ntridec-(NLys-Nspe-Nspe(p-Br))$_2$-NLys-NH$_2$ | | |
| MXB022 | H-(NLys-Nssb-Nssb)$_4$-NH$_2$ | | |

Regarding herpesvirus infections in particular, it is notable that these infections are common and easily transmissible. However, due to its mechanism of infection and pathogenesis, it has been difficult to design any effective vaccines to prevent herpesvirus infections. Furthermore, the development of other preventive and palliative methods has proven to be challenging. Since AMPs exhibit potent activity against HSV-1, their potential as an antiviral preventive or therapeutic agent is significant. However, direct introduction of the peptides has not translated into an effective treatment due, for example, to high cost, molecular instability, and unknown pharmacokinetics. A novel approach is disclosed herein for the treatment of herpesvirus infections which involves the use of peptoids. This approach is advantageous in numerous ways.

First of all, peptoids are a different class of antimicrobials, and preliminary data shows that they exhibit potent activity against HSV-1. Based on data showing the mechanism of action of LL-37 against KSHV, the current investigators believe that these peptoids exhibit a novel mechanism of action against viruses. This approach thus demonstrates a new paradigm in antiviral drug design.

Secondly, peptoids may be applied clinically as an effective medical therapy to treat HSV infections, or as a pre- Example 1

This example illustrates the surprising efficacy of several peptoids against the HSV-1 virus.

A series of 9 peptoids were tested for activity against HSV-1. The peptoids were incubated with 10$^5$ pfu HSV-1 GFP for 2 hours at 37° C. Virus was added to triplicate cultures of OKF6/TERT-1 cells (oral keratinocytes) at an MOI of 0.01:1, and incubated for a further 24 hours at 37° C. Total DNA was isolated from the cultures, and relative HSV-1 DNA levels were quantified by QPCR relative to genomic β-actin.

The results are shown in FIG. 2. As seen therein, there was varied activity among the peptoids against HSV-1.

Example 2

This example illustrates the time and dose-dependence of peptoids against HSV-1.

Select peptoids from EXAMPLE 1 were for activity against HSV-1 in time- and dose-response assays. These peptoids were tested at 5 and 20 µg/ml for 2 hr at 37° C. (FIG. 3) or at 20 µg/ml for 0-120' at 37° C. (FIG. 4) prior to infection of OKF6-TERT-1 cells in triplicate. The samples were subjected to quantification as in EXAMPLE 1.

Figure 3:
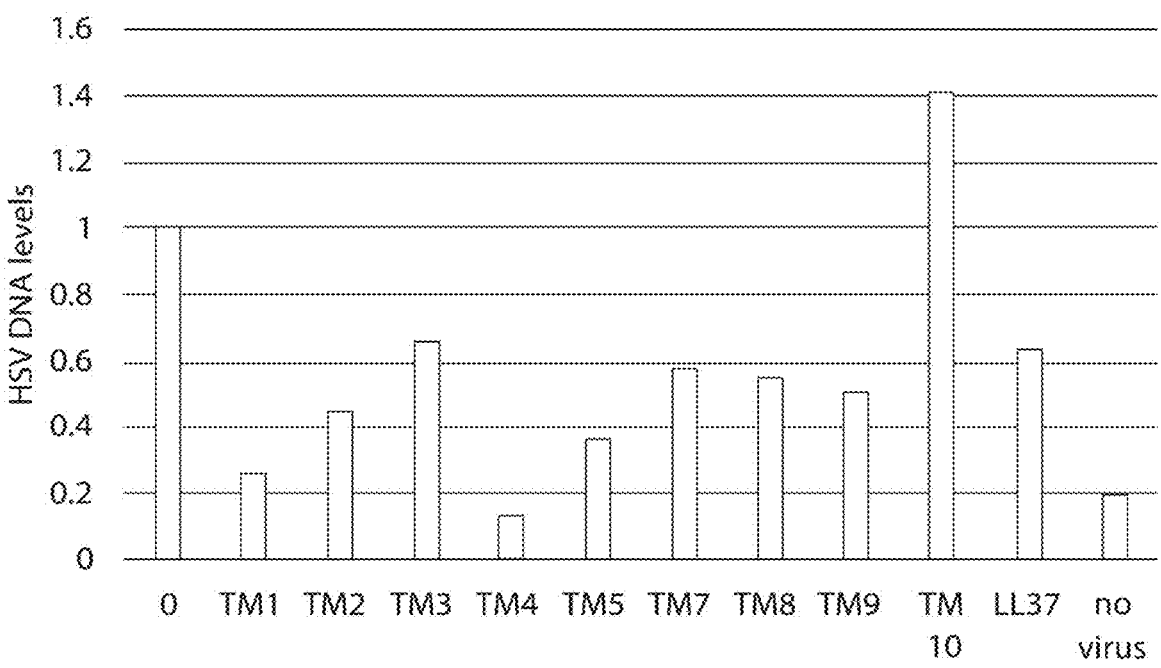
FIG. 3 is a chart illustrating the efficacy of various peptoids against HSV-1 virus, as compared to LL-37 and a control (no virus).
Figure 4:
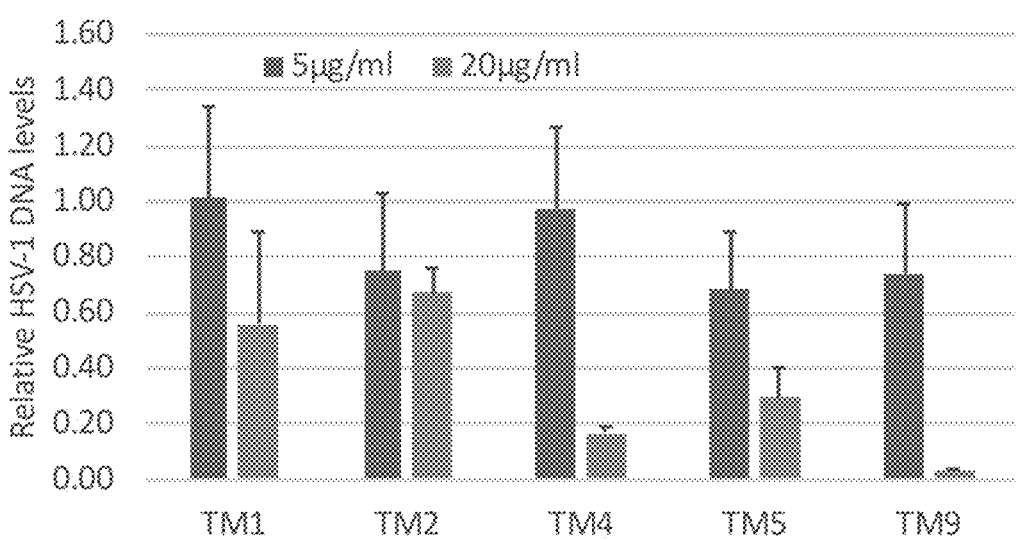
FIGS. 4-5 are charts depicting the time and dose-dependence of peptoids against HSV-1.

The results in FIGS. 3-4 demonstrate that the activity can be observed as early as 30' at 20 µg/ml, and with 5 µg/ml at 2 hr incubation. Together, the results suggest that peptoids may be developed as antiviral agents against HSV-1.

Example 3

This example illustrates in vivo activity of a peptoid of the type disclosed herein in a mouse model.

A study was conducted in which a novel lung infection model was utilized to assess the in vivo efficacy of a peptoid of the type disclosed herein. In this study, *P. aeruginosa* expressing a bioluminescent marker was infected into mice by intratracheal inoculation. The strain was inoculated at a level of $10^7$ cfu into mice (n=8), followed by delivery of 20 µl of the peptoid TM5 at a concentration of 40 µg/ml after 2 hours. After 24 hours, the bioluminescence was quantified ($p<0.05$) by in vivo imaging (IVIS, Perkin-Elmer). The results are shown in FIGS. 5-6.

Figure 5:
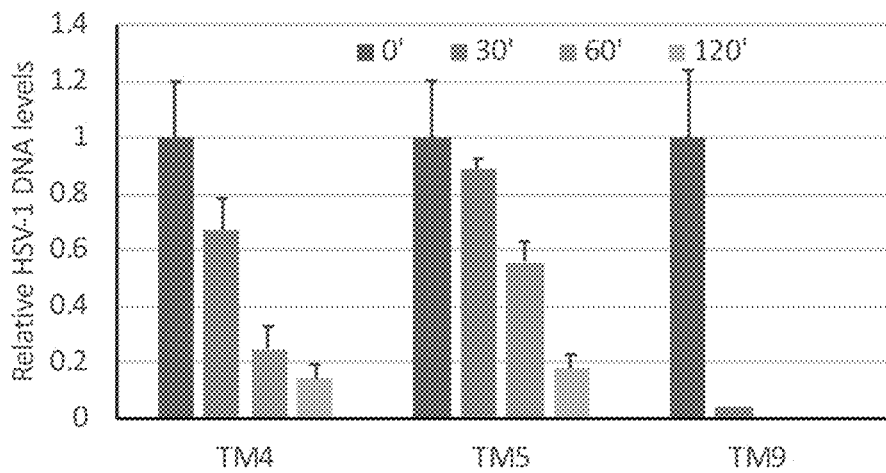
Figure 6:
FIG. 6 is a bioluminescent image depicting the activity of peptoids in vivo in a mouse model.

As seen in FIG. 5, a clear reduction in luminescent bacteria was observed in the treated mice (on the left) compared to the untreated mice (right). These results are quantified in FIG. 6. This results demonstrate that the peptoids retain their ability to bind and inactivate microbes in an in vivo environment, thus supporting the hypothesis that they will also retain antiviral activity.

Example 4

This example illustrates in vitro toxicity of peptoids of the type disclosed herein.

To quantify the cytotoxicity of the peptoids disclosed herein, 3-dimensional cultures of oral epithelial cells (Mat-Tek) were treated with three of these peptoids (MXB004, MXB005 and MXB006) at increasing concentrations for 3 hours. In particular, 100 µl samples of the peptoids were incubated on the apical surface of triplicate EpiOral cultures (MatTek) for 3 hours at increasing concentrations. Cell viability was immediately quantified after incubation by MTT assay.

Figure 7:
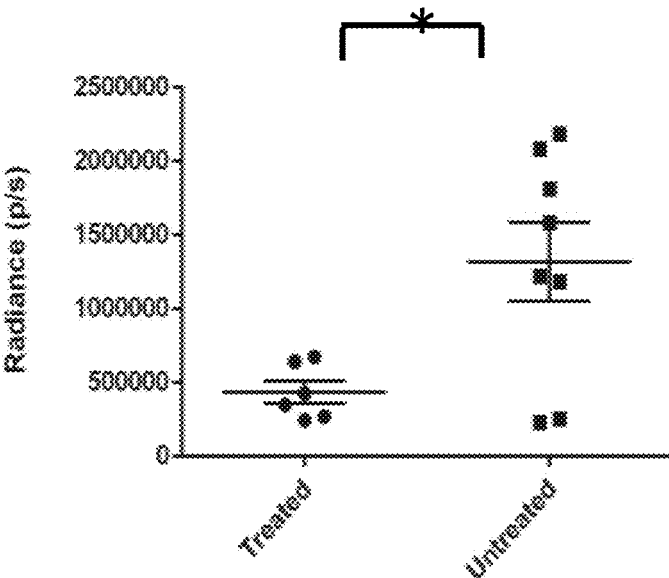
FIG. 7 is a graph depicting the activity of peptoids in vivo in a mouse model.
Figure 8:
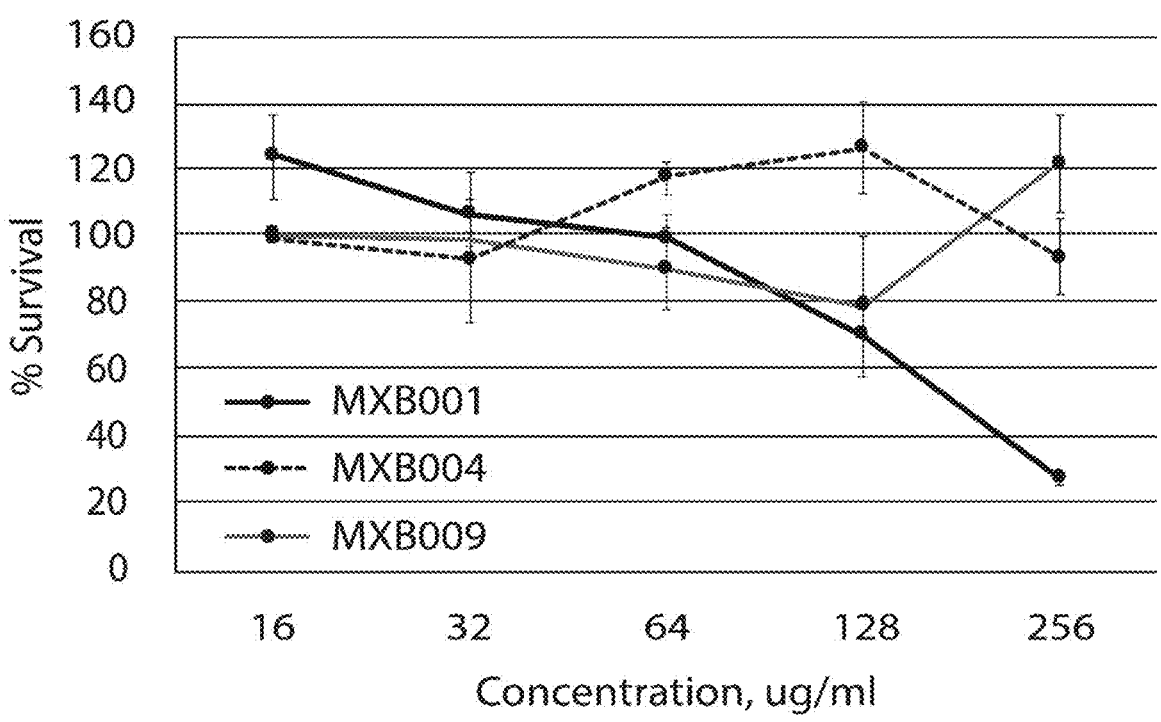
FIG. 8 is a graph depicting 3D tissue culture toxicity for three peptoids (MXB-001, MXB-004 and MXB-009) of the type disclosed herein.
Figure 9:
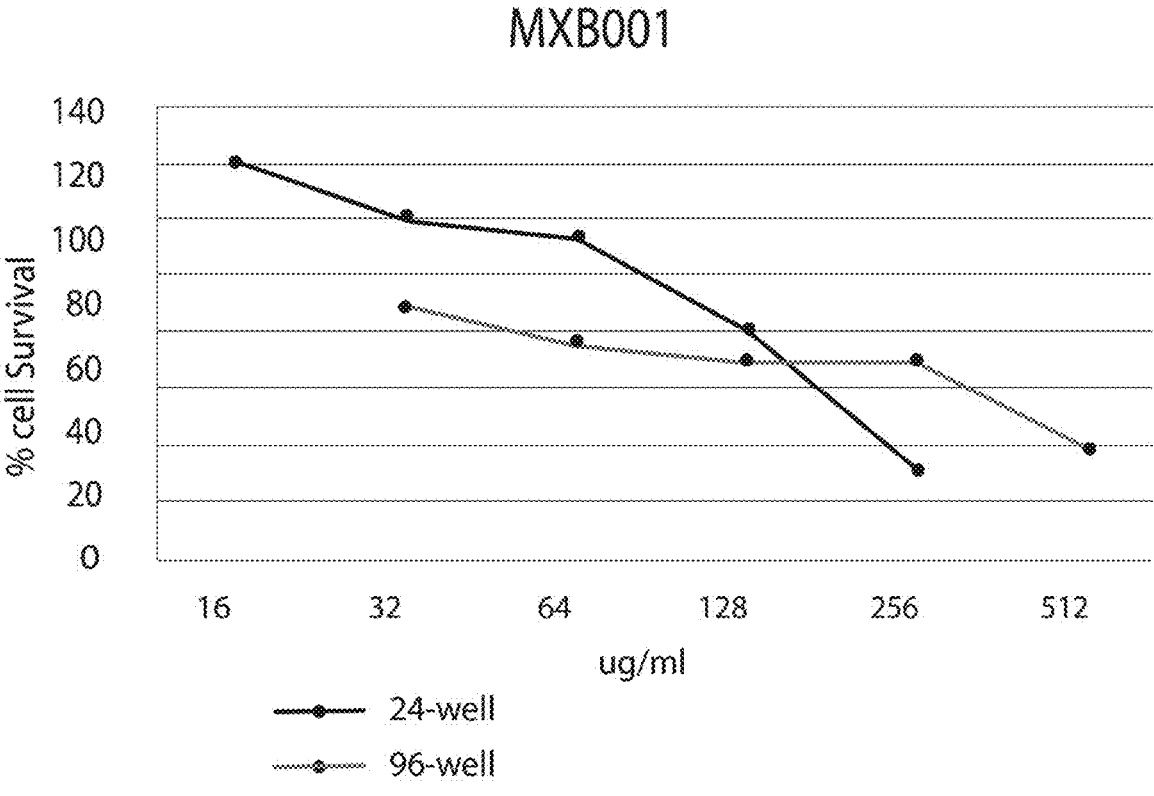
FIGS. 9-14 are graphs depicting the results of toxicity testing for a series of peptoids of the type disclosed herein.
Figure 10:
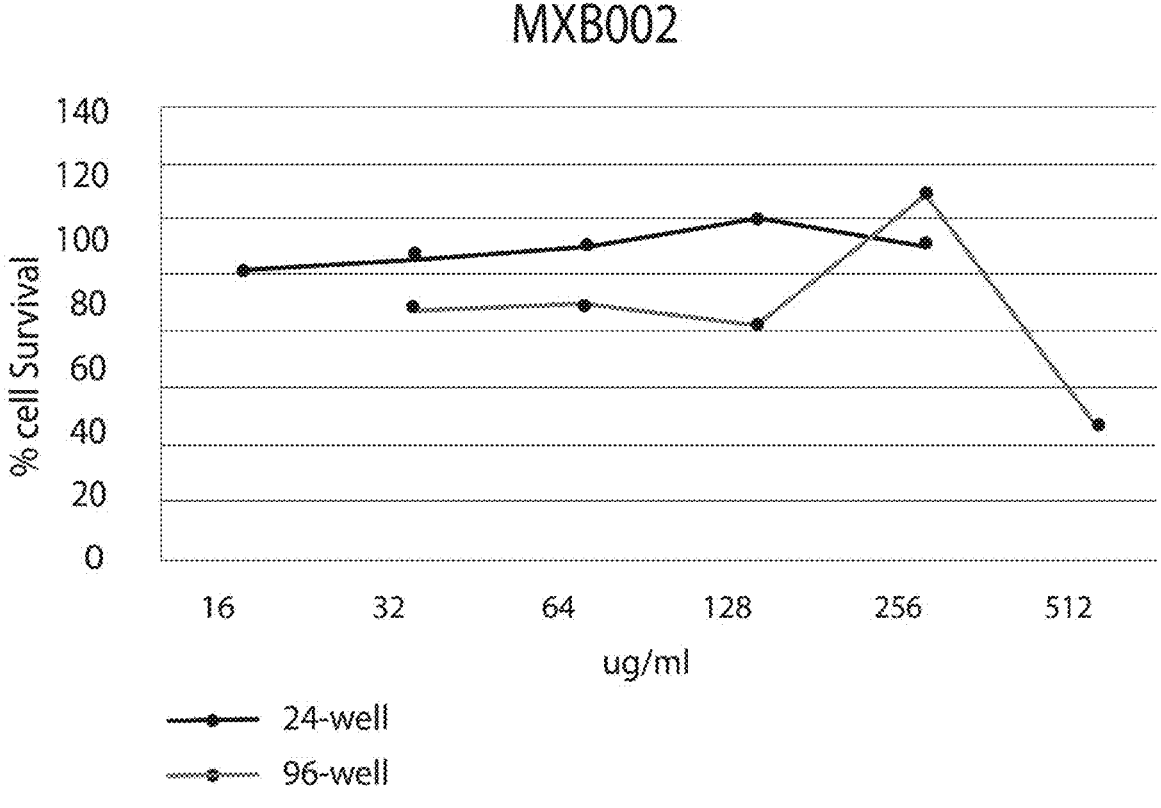
Figure 11:
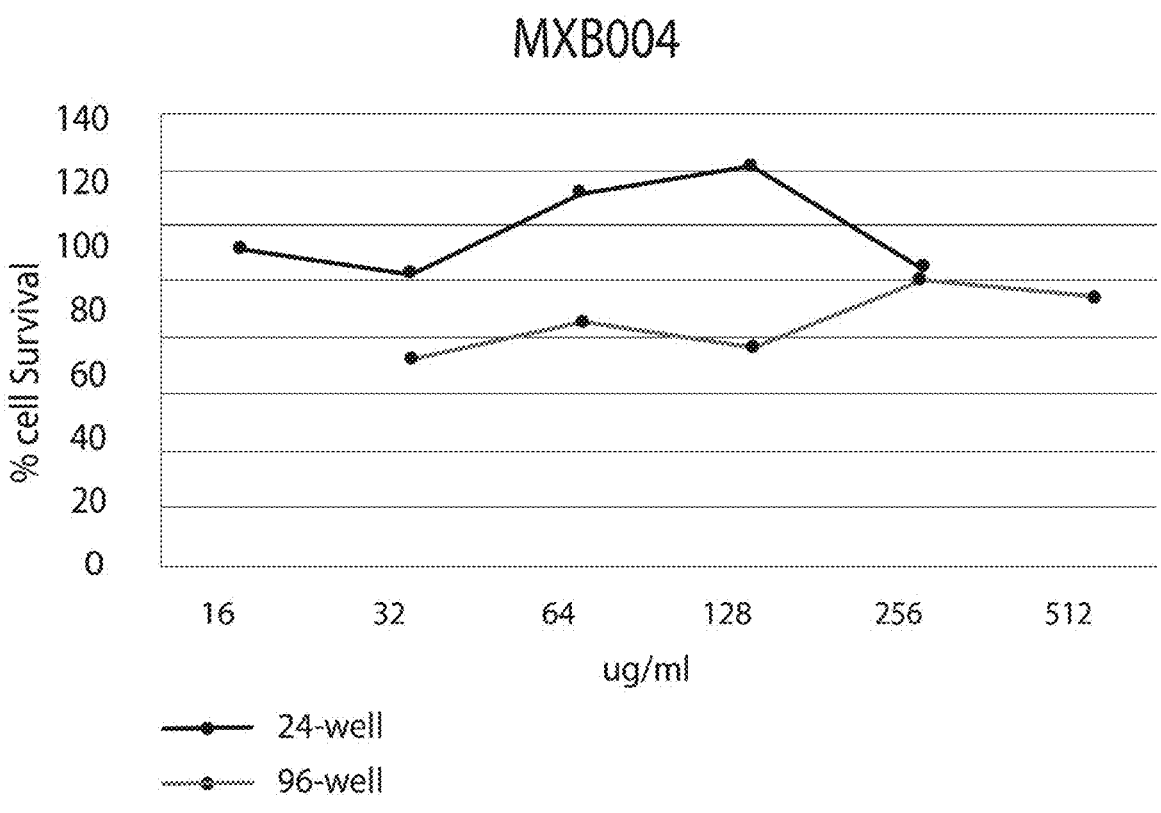
Figure 12:
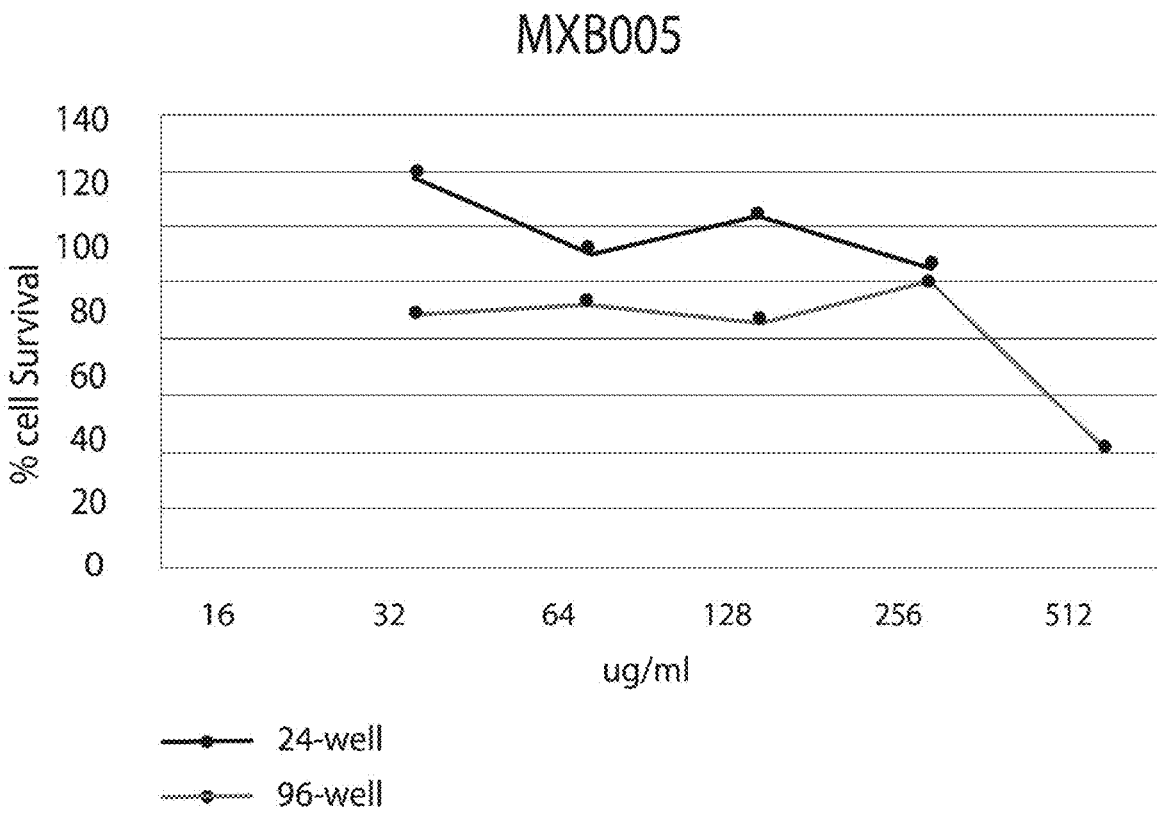
Figure 13:
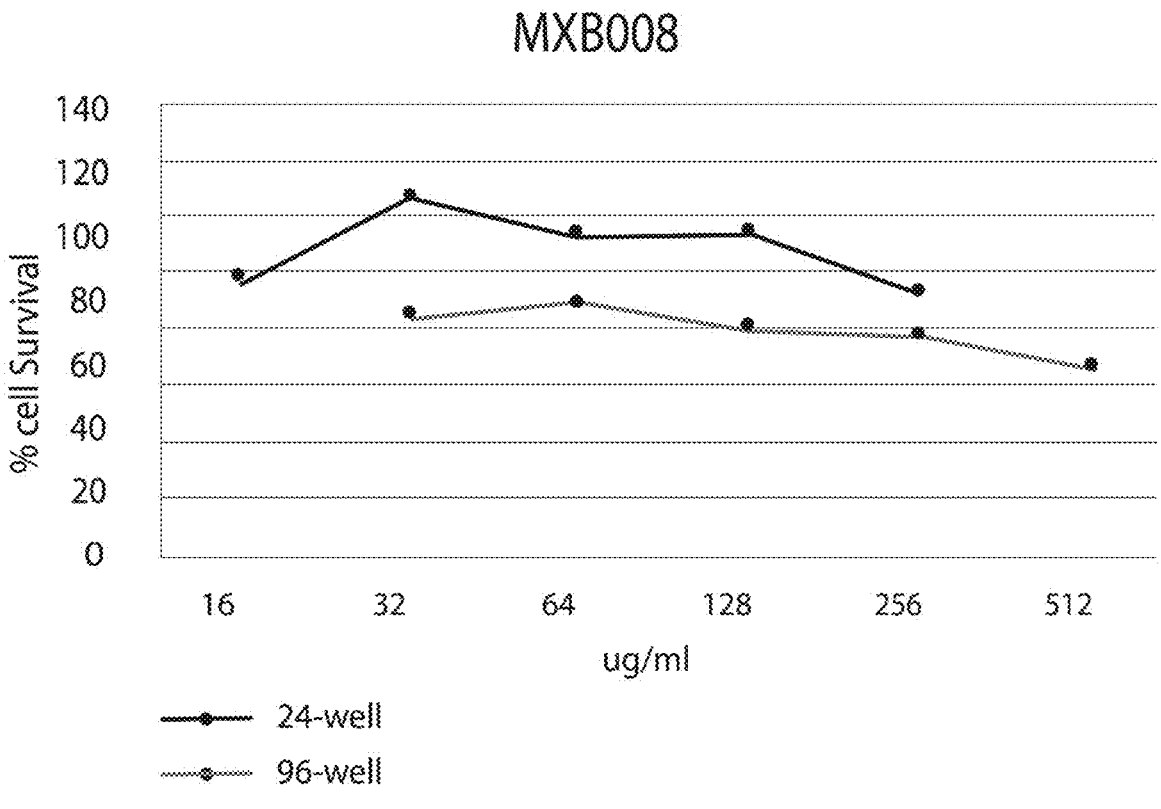
Figure 14:
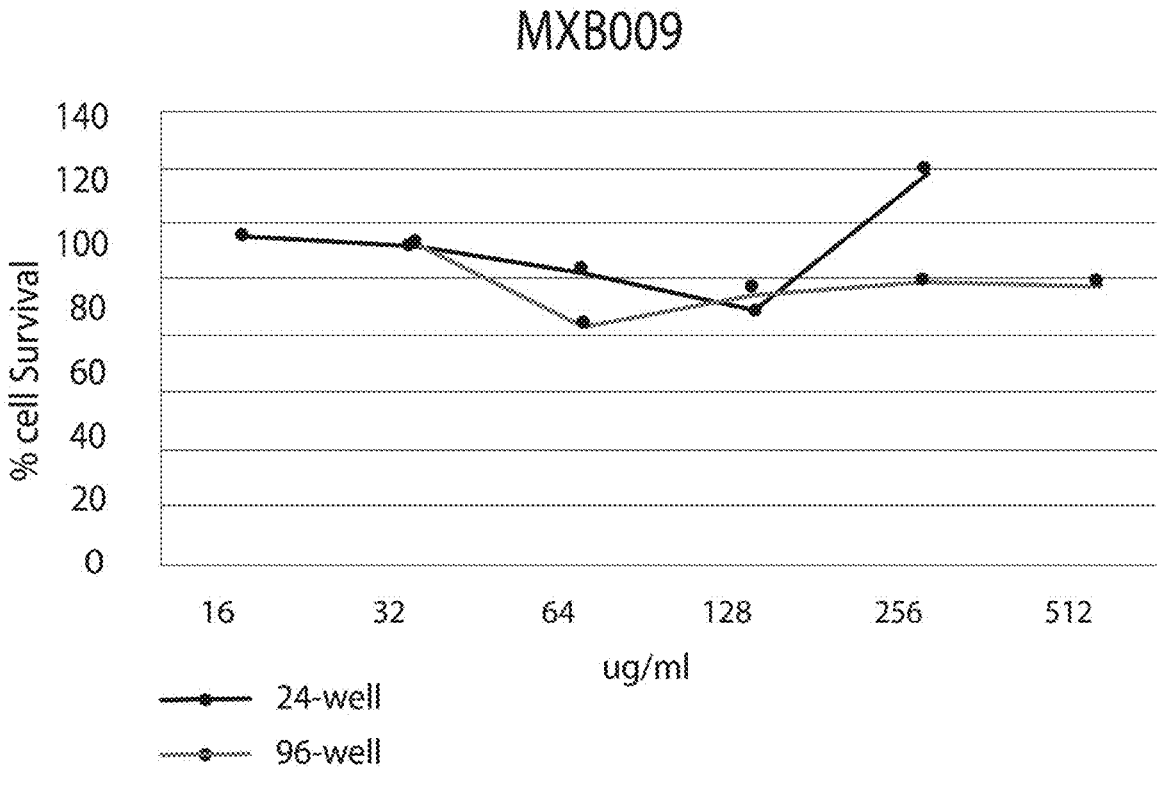
Figure 15:
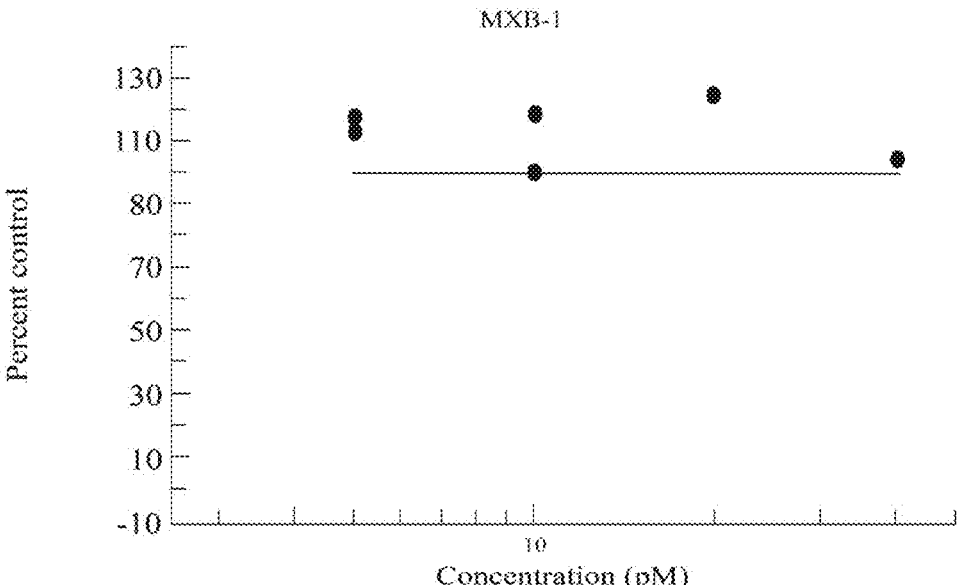
Figure 16:
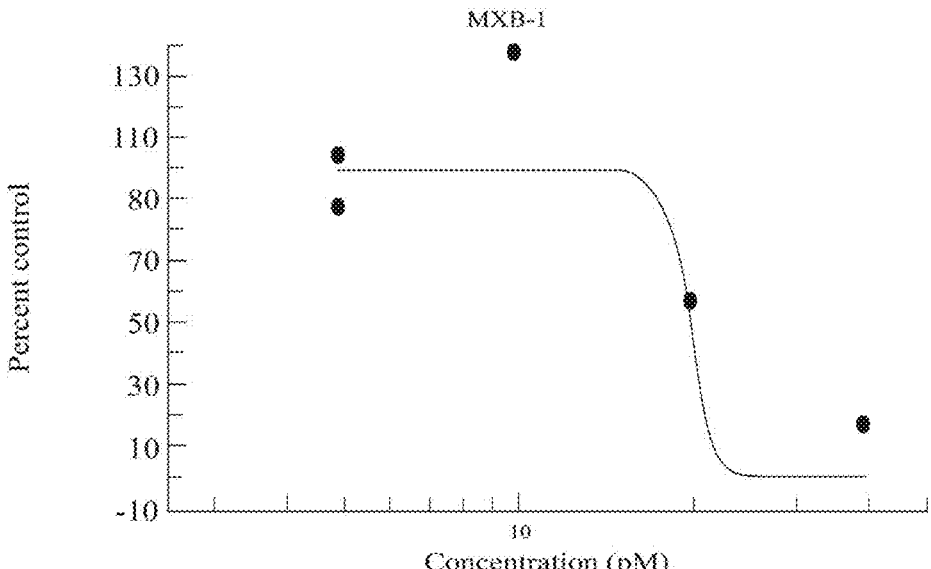
Figure 23:
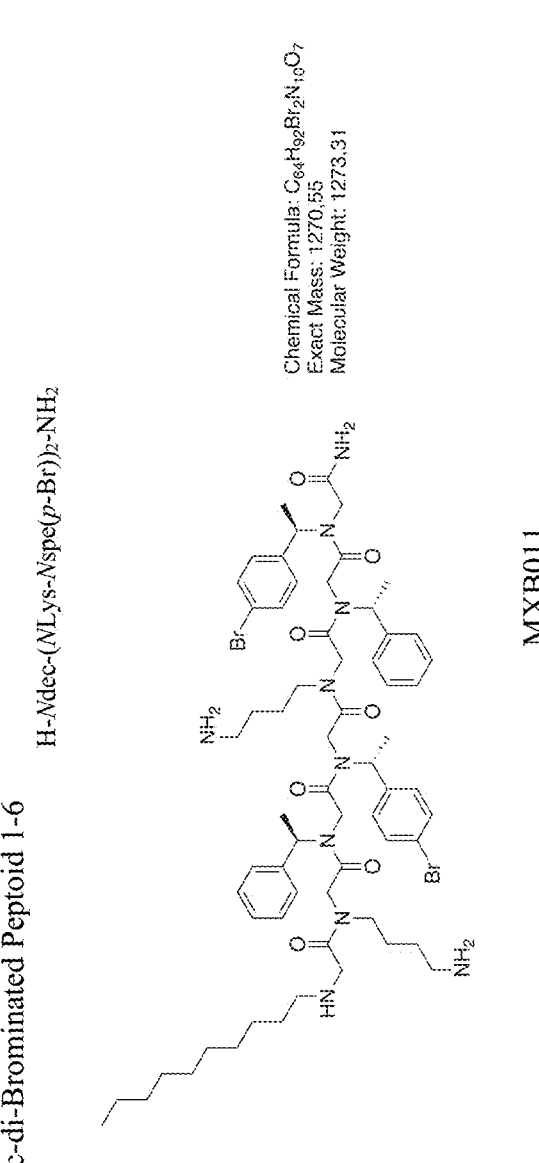
Figure 24:
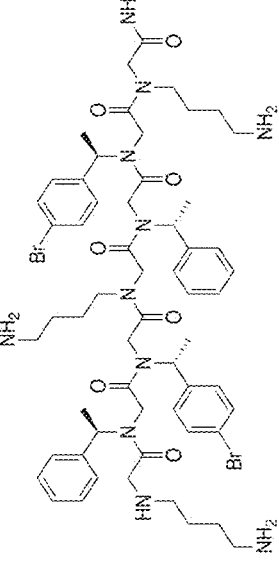
Figure 26:
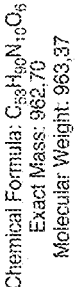
Figure 26:
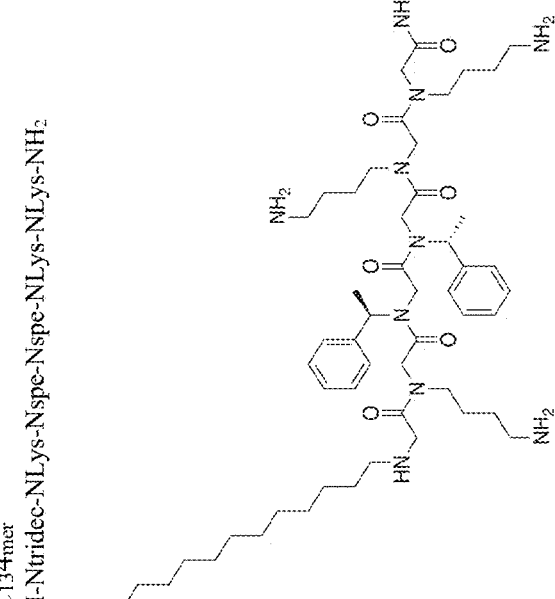
Figure 27:
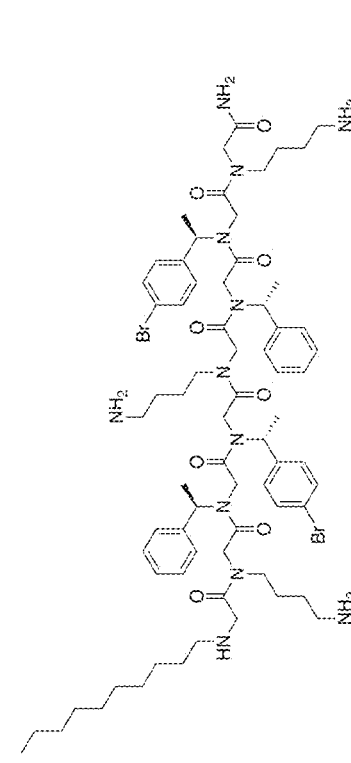

The results are shown in FIG. 7, which depicts the mean % survival+/−SD. These results demonstrate that there was no toxicity of the peptoids at any concentration below 256 µg/ml.

Example 5

This example illustrates in vivo toxicity of peptoids of the type disclosed herein.

While in vitro studies demonstrated that TM5 exhibits an LD50 against established cell lines of 40-10004, studies suggest that the peptoids may be less toxic in vivo. As part of a study on antimicrobial activity of these peptoids in the airway, Balb/c mice were treated intratracheally with 20 µl of 40 µg/ml (42 µM) or 80 µg/ml (8404) of TM5, and monitored for 48 hours following treatment for signs of toxicity.

The results are depicted in FIG. 7. As indicated therein, no adverse effects were found, as measured by either survival of all animals, or by Karnofsky score based on activity, weight loss, respiration, and appearance of the animals. These results are strongly supportive of the proposition that the peptoid will not be toxic in topical delivery to the lip.

Example 6

This example illustrates in vivo toxicity of peptoids of the type disclosed herein.

To better model in vivo conditions in assessing toxicity, several of the peptoids disclosed herein were evaluated in a 3D tissue model. EpiAirway prepared ALI plates were purchased from MatTek Life Sciences. Tissues were shipped overnight and allowed to acclimate for 24 hours prior to initiation of testing. The study was performed in the Diamond Laboratory, at the University of Louisville School of Dentistry, Department of Oral Immunology and Infectious Diseases. Toxicity was assessed utilizing MTT assays from 16 ug/mL to 256 ug/mL for each compound.

The tissue preparation was as follows:
1. In a tissue culture hood, using sterile technique dispense 250 µl of cold ALI medium into each well of plate provided.
2. While the package is still cold, transfer one tissue insert to each well of the plate containing media (from the preceding step). The apical surface of the tissue remained exposed to air (i.e. media was not added to the inside of the insert).
3. Equilibrate the tissues overnight (16-18 hours) in the media at 37° C., 5% CO2.
4. At the end of the equilibration period, aspirate the media from each well and replace with fresh, pre-warmed media. (Tissues are now ready for the experiment.)

The peptoid testing procedure was as follows:
1. Remove media from wells.
2. Wash 1× with PBS.
3. Apply peptoids to each well in 100 uL of PBS (cation-free). Use 2-fold dilutions of peptoid with concentrations starting at 256 ug/mL. For ALI cultures, add 100 uL to the apical chamber. Perform all conditions in triplicate and include negative controls without peptoid in triplicate.
4. Incubate at 37° C. for 3 hours.
5. Remove peptoid from wells and wash 3× with PBS.

The MTT assay assessment was performed as follows:
1. Dispense 100 µl of the MTT reagent into the appropriate number of wells of the feeder plate.
2. Gently aspirate any remaining test material.
3. Rinse each tissue three times by gentle application and removal of 150 µl of PBS with a pipette.
4. Place the rinsed inserts into the wells containing pre-warmed MTT reagent and incubate at 37° C., 5% CO2 for 1.5 hours. Viable tissues will convert the MTT to a purple dye. The amount of conversion is proportional to the viability of the tissue.
5. Following the 1.5 hour incubation, remove the inserts from the MTT solution and blot the underside of the wells on a paper towel.

The results are depicted in FIGS. 8-13. As seen therein, the peptoids tested exhibited low toxicity across a range of concentrations.

Example 7

This example illustrates the efficacy of peptoids of the type disclosed herein on SARS-CoV-2.

This study was conducted in vitro to determine the efficacy of MXB-001 and MXB-004 on SARS-CoV-2. It was performed using Vero E6 and SARS-CoV-2 Isolate. Vero E6 (ATCC CRL-1586) was purchased from ATCC and maintained in DMEM with 10% FBS. Cells were passaged weekly. SARS-CoV-2 Isolate USA-WA1/2020 was obtained from BEI Resources and amplified once in Vero E6 cells. Peptoid compounds (non-GMP) were synthesized using solid-state synthesis, purified with reversed phase HPLC and were received in hydrochloride form. Dilutions were made utilizing cation-free PBS.

Peptoids diluted in serum-free media were mixed with diluted virus that can produce 40-50 plaques in a well of 12-well plate, then incubated for two hours at 37° C. Vero E6 Cells grown in 12-well plates were infected with the virus-peptoid mixture for one hour at 37° C. with 5% $CO_2$ with rocking every 20 min. Cells were covered with 1 mL of an overlay media (1×DMEM with 0.8% Avicel and 5% FBS) and further cultured for three days. Cells were fixed with 2% paraformaldehyde and plaques by CPE were visualized by a counter-staining with 0.4% crystal violet, and the number of plaques were counted. Plaque assay was carried out on supernatants. The results are depicted in TABLE 2 below:

TABLE 2

Plaque Assay Results

| Compound | Conc. (µg/ml) | Count | % control |
|---|---|---|---|
| MXB-001 | 40 | 46 | 104.55 |
| | 40 | 46 | 104.55 |
| | 20 | 55 | 125 |
| | 20 | 55 | 125 |
| | 10 | 44 | 100 |
| | 10 | 52 | 118.18 |
| | 5 | 52 | 118.18 |
| | 5 | 50 | 113.64 |
| MXB-004 | 40 | 7 | 15.91 |
| | 40 | 7 | 15.91 |
| | 20 | 24 | 54.55 |
| | 20 | 25 | 56.82 |
| | 10 | 60 | 136.36 |
| | 10 | 59 | 134.09 |
| | 5 | 38 | 86.36 |
| | 5 | 45 | 102.27 |

As seen therein, the peptoids tested exhibited good efficacy against SARS-CoV-2 across a range of concentrations.

Various peptoids and oligomers of N-substituted glycines may be utilized in accordance with the teachings herein to make antiviral pharmaceutical compositions and treatments. In addition to the peptoids set forth in TABLE 1, these include the peptoids described in U.S. Pat. No. 8,445,632 (Barron et al.), which is incorporated herein by reference in its entirety, as well as the peptoids disclosed in U.S. Pat. No. 9,938,321 (Kirshenbaum et al.), U.S. Pat. No. 9,315,548 (Kirshenbaum et al.) and U.S. Pat. No. 8,828,413 (Kirshenbaum et al.), all of which are incorporated herein by reference in their entirety.

Various halogenated peptoids and halogenated oligomers of N-substituted glycines may also be utilized in accordance with the teachings herein to make antiviral pharmaceutical compositions and treatments. These include, without limitation, various halogenated analogs of the foregoing peptoids and oligomers of N-substituted glycines. These halogenated compositions may be halogenated in various ways. For example, these compounds may include any number of halogen substitutions with the same or different halogens. In particular, these compounds may include one or more fluoro-, chloro-, bromo- or iodo-substitutions, and may include substitution with two or more distinct halogens. However, the use of one or two bromo- or chloro-substitutions is preferred in many applications. Moreover, while the peptoids described herein may be halogenated at various locations, para halogenation on the peptoids containing aryl rings is especially preferred in many applications, although ortho- and meta-substitution, or even perhalogentation, may be useful in some applications.

The compositions described herein may also be alkylated, and preferably have terminal alkylation. Here, alkylation (and especially terminal alkylation) with a C10 or C13 tail is especially preferred. It has been found that such terminal alkylation can dramatically enhance the antibacterial activity of a peptoid, and in some cases, may cause a peptoid which otherwise has low antibacterial activity to have significant antibacterial activity.

The pharmaceutical compositions utilized in the systems and methodologies disclosed herein may utilize one or more active ingredients which may be dissolved, suspended or disposed in various media. Such media may include, for example, various liquid, solid or multistate media such as, for example, emulsions, gels or creams. Such media may include liquid media, which may be hydrophobic or may comprise one or more triglycerides or oils. Such media may include, but is not limited to, vegetable oils, fish oils, animal fats, hydrogenated vegetable oils, partially hydrogenated vegetable oils, synthetic triglycerides, modified triglycerides, fractionated triglycerides, and mixtures thereof. Triglycerides used in these pharmaceutical compositions may include those selected from the group consisting of almond oil; babassu oil; borage oil; blackcurrant seed oil; black seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; and mixtures thereof. The use of coconut oil is especially preferred.

Various fatty acids may be utilized in the pharmaceutical compositions disclosed herein. These include, without limitation, both long and short chain fatty acids. Examples of such fatty acids include, but are not limited to, docosahexaenoic acid, caprylic acid, capric acid, lauric acid, butyric acid, and pharmaceutically acceptable salts thereof.

The pharmaceutical compositions disclosed herein may be applied in various manners. Thus, for example, these compositions may be applied as oral, transdermal, transmucosal, intravenous or injected treatments, or via cell-based drug delivery systems. Moreover, these compositions may be applied in a single dose, multi-dose or controlled release fashion.

The pharmaceutical compositions disclosed herein may be manufactured as tablets, liquids, gels, foams, ointments or powders. In some embodiments, these compositions may be applied as microparticles or nanoparticles.

Various counterions may be utilized in forming pharmaceutically acceptable salts of the materials disclosed herein. One skilled in the art will appreciate that the specific choice of counterion may be dictated by various considerations. However, the use of sodium and hydrochloride salts may be preferred in some applications.

In some embodiments, the compositions described herein may be formulated as mixtures of two or more peptoids. These mixtures may feature peptoids in various ratios. For example, in some embodiments, a first peptoid with higher antiviral efficacy but higher cytotoxicity may be mixed with a second peptoid of lower antiviral efficacy and lower cytotoxicity to produce a mixture with acceptable levels of efficacy and cytotoxicity.

In some embodiments, the peptoids disclosed herein may be utilized to treat a subject for an infection involving at least one viral pathogen and at least one bacterial pathogen. In such cases, the peptoid may be effective in simultaneously treating both pathogens. A wide variety of tissues infected with both types of pathogens may be treated with the compositions and methodologies disclosed herein. These include, without limitation, the tissues of the ear, nose, sinus, throat, mouth, lungs and vagina, as well as the tissues of the urethral tracts. Such infections may include, without limitation, those accompanying sexually transmitted diseases (STDs).

The Use of Peptoid Designations

The above description of the present invention is illustrative, and is not intended to be limiting. It will thus be appreciated that various additions, substitutions and modifications may be made to the above described embodiments without departing from the scope of the present invention.

Accordingly, the scope of the present invention should be construed in reference to the appended claims. For convenience, some features of the claimed invention may be set forth separately in specific dependent or independent claims. However, it is to be understood that these features may be combined in various combinations and subcombinations without departing from the scope of the present disclosure. By way of example and not of limitation, the limitations of two or more dependent claims may be combined with each other without departing from the scope of the present disclosure.

What is claimed is:

1. A method for treating a subject for a *Herpes* simplex virus type 1 (HSV-1) infection, comprising:

administering to the subject a pharmaceutically effective amount of a poly-N-substituted glycine compound, wherein the poly-N-substituted glycine compound is selected from the group consisting of H-(NLys-Nspe-Nspe)$_4$-NH$_2$, H-(NLys-Nspe-Nspe (p-Br))$_2$—NH$_2$, H-NLys-Nspe-Nspe-NLys-Nspe-Nspe(p-Br)-NH$_2$, H-((NLys-Nspe(p-Br)-Nspe(p-Br))2-NH$_2$, H-Ntridec-NLys-Nspe-Nspe-NLys-NH$_2$, H-(NLys-Nspe-Nspe)$_3$-NLys-Nspe-NH$_2$, H-(NLys-Nspe-Nspe)$_2$-NH$_2$, and H-Ndec-(NLys-Nspe-Nspe)$_2$-NH$_2$.

\* \* \* \* \*